US005981840A

United States Patent [19]
Zhao et al.

[11] Patent Number: 5,981,840
[45] Date of Patent: Nov. 9, 1999

[54] METHODS FOR AGROBACTERIUM-MEDIATED TRANSFORMATION

[75] Inventors: Zuo-Yu Zhao; Weining Gu; Tishu Cai; Dorothy A. Pierce, all of Urbandale, Iowa

[73] Assignee: Pioneer Hi-Bred International, Inc., Des Moines, Iowa

[21] Appl. No.: 08/788,018

[22] Filed: Jan. 24, 1997

[51] Int. Cl.$^6$ ............... C12N 15/00; C12N 15/05; C12N 15/84; A01H 5/00

[52] U.S. Cl. ............... 800/294; 800/278; 435/468; 435/419; 435/320.1

[58] Field of Search ............... 800/205, 250, 800/294, 278; 435/172.3, 172.1, 468, 419, 320.1; 47/58, DIG. 1

[56] References Cited

U.S. PATENT DOCUMENTS

| | | | |
|---|---|---|---|
| 5,164,310 | 11/1992 | Smith et al. | 435/172.3 |
| 5,177,010 | 1/1993 | Goldman et al. | 435/172.3 |
| 5,384,253 | 1/1995 | Krzyzek et al. | 435/172.3 |
| 5,591,616 | 1/1997 | Hiei et al. | 435/172.3 |

FOREIGN PATENT DOCUMENTS

| | | |
|---|---|---|
| 586 355 A2 | 3/1994 | European Pat. Off. . |
| 604 662 A1 | 7/1994 | European Pat. Off. . |
| 672 752 A1 | 9/1995 | European Pat. Off. . |
| 687 730 A1 | 12/1995 | European Pat. Off. . |
| 4-222527 | 8/1992 | Japan . |
| 2 211 204 | 6/1989 | United Kingdom . |
| WO 91/02071 | 2/1991 | WIPO . |
| WO 92/09696 | 6/1992 | WIPO . |
| WO 95/10178 | 4/1995 | WIPO . |

OTHER PUBLICATIONS

Shillito, R.D., Carswell, G.K., and Kramer, C., "Maize Protoplast Culture" in *The Maize Handbook*, Springer–Verlag, NY, pp. 696 line 2 (1994).

Ritchie et al., "*Agrobacterium tumefaciens*–mediated expression of gusA in maize tissues", *Transgenic Research* 2, 252–265 (1993).

Songstad et al., "Establishment of friable embryogenic (type II) callus from immature tassels of *zea mays* (poaceae)", *American Journal of Botany* 79–7, 761–764 (1992).

Maize Genetics Cooperative Newsletter (No. 70), 63 (1996).

R.L. Phillips et al., "Cell/Tissue Culture and In Vitro Manipulation" in *Corn and Corn Improvement, Third Edition;* Sprague et al., eds.; American Society of Agronomy, Inc., Crop Science Society of America, Inc., Soil Science Society of America, Inc.: Madison, WI; pp. 345–387 (1988).

G. Donn et al., "Stable transformation of Maize with a chimaeric, modified Phosphinothricin–acetyltransferase gene from *Streptomyces viridochromogenes*", *Abstracts of the VIIth International Congress on Plant Cell and Tissue Culture*, Abstract #A2–38, p. 53 (1990).

An et al., "Functional Analysis of the 3' Control Region of the Potato Wound–Inducible Proteinase Inhibitor II Gene", *The Plant Cell*, 1, 115–122 (1989).

Armstrong et al., "Development and availability of germplasm with high Type II culture formation response" *Maize Genetics Cooperation Newsletter*, 65, 92–93 (1991).

Armstrong et al., "Genetic control of plant regeneration from maize tissue cultures", *Maize Genetics Cooperation Newsletter*, 59, 92–93 (1985).

Bytebier et al., "T–DNA organization in tumor cultures and transgenic plants of the monocotyledon *Asparagus officinalis*", *Proc. Natl. Acad. Sci. USA*, 84 5345–5349 (1987).

Chih–ching, "The $N_6$ Medium and its Applications to Anther Culture of Cereal Crops"; *Proc. Symp. Plant Tissue Culture;* Science Press: Peking, pp. 43–50 (1978).

Chilton, "Agrobacterium gene transfer: Progress on a 'poor man's vector' for maize", *Proc. Natl. Acad. Sci. USA*, 90, 3119–3120 (1993).

Christensen et al., "Maize polyubiquitin genes: structure, thermal perturbation of expression and transcript splicing, and promoter activity following transfer to protoplasts by electroporation", *Plant Mol. Biol.*, 18, 675–689 (1992).

Ditta et al., "Broad host range DNA cloning system for Gram–negative bacteria: Construction of a gene bank of Rhizobium meliloti", *Proc. Natl. Acad. Sci. USA*, 77, 7347–7351 (1980).

Dennehey et al., "Comparison of selective agents for use with the selectable maker gene bar in maize transformation", *Plant Cell, Tissue and Organ Culture*, 36, 1–7 (1994).

Dennis et al., "Molecular analysis of the alcohol dehydrogenase (Adh1) gene of maize", *Nucleic Acids Research*, 12, 3983–4000 (1984).

Duncan et al., "The production of callus capable of plant regeneration from immature embryos of numerous *Zea mays* genotypes", *Planta*, 165, 322–332 (1985).

Gallie et al., "The 5'–leader sequence of tobacco mosaic virus RNA enhances the expression of foreign gene transcripts in vitro and in vivo", *Nucl. Acids Research*, 15, 3257–3273 (1987).

Gardner et al., "The complete nucleotide sequence of an infectious clone of cauliflower mosaic virus by M13mp7 shotgun sequencing", *Nucl. Acids Research*, 9, 2871–2888 (1981).

(List continued on next page.)

*Primary Examiner*—Gary Benzion
*Attorney, Agent, or Firm*—Pioneer Hi-Bred International, Inc.

[57] ABSTRACT

The present invention relates to methods for improving the transformation frequency of Agrobacterium-mediated transformation of maize embryos. A preferred method for transforming maize using Agrobacterium comprises the steps of: contacting at least one immature embryo from a maize plant with Agrobacterium capable of transferring at least one gene to said embryo; co-cultivating the embryos with Agrobacterium; culturing the embryos in medium comprising N6 salts, an antibiotic capable of inhibiting the growth of Agrobacterium, and a selective agent to select for embryos expressing the gene; and regenerating plants expressing the gene.

62 Claims, 3 Drawing Sheets

OTHER PUBLICATIONS

Gould et al., "Transformation of *Zea mays* L. Using *Agrobacterium tumefaciens* and the Shoot Apex", *Plant Physiol.*, 95 426–434 (1991).

Green et al., "Plant Regeneration from Tissue Cultures of Maize", *Crop Sci.*, 15 417–421 (1976).

Grimsley et al., "Agrobacterium–mediated delivery of infectious maize streak virus into maize plants", *Nature*, 325, 177–179 (1987).

Herrera–Estrella et al., "Chimeric genes as dominant selectable markers in plant cells", *EMBO J.*, 2, 987–995 (1983).

Hood et al., "T–DNA and Opine Synthetic Loci in Tumors Incited by *Agrobacterium tumefaciens* A281 on Soybean and Alfalfa Plants", *J. Bacteriol.*, 168, 1283–1290 (1986).

Hood et al., "Restriction Endonuclease Map of pTi Bo542, A Potential Ti Plasmid Vector for Genetic Engineering of Plants", *BioTechnology*, 702–709–(1984).

Hooykaas, "Transformation of plant cells via Agrobacterium", *Plant Mol. Bio.*, 13, 327–336 (1989).

Horsch et al., "Inheritance of Functional Foreign Genes in Plants", *Science*, 223, 496–498 (1984).

Ishida et al., "High efficiency transformation of maize (*Zea mays* L.) mediated by *Agrobacterium tumefaciens*", *Nature Biotech.*, 14, 745–750 (1996).

Jefferson et al., "β–Glucuronidase from *Escherichia coli* as a gene–fusion marker", *Proc. Natl. Acad. Sci. USA*, 83, 8447–8451 (1986).

Jin et al., "Genes Responsible for the Supervirulence Phenotype of *Agrobacterium tumefaciens* A281", *J. Bacteriol.*, 169, 4417–4425 (1987).

Kamo et al., "Regeneration of *Zea Mays* L. From Embryogenic Callus", *Bot. Gaz.*, 146, 327–334 (1985).

Komari et al., "Physical and Functional Map of Supervirulent *Agrobacterium tumefaciens* Tumor–Inducing Plasmid pTiBo542", *J. Bacteriol.*, 166, 88–94 (1986).

Komari et al., "Transformation of cultured cells of *Chenopodium quinoa* by binary vectors that carry a fragment of DNA from the virulence region of pTiBo542", *Plant Cell Reports*, 9, 303–306 (1990).

Komari et al., "Vectors carrying two separate T–DNAs for co–transformation of higher plants mediated by *Agrobacterium tumefaciens* and segregation of transformants free from selection markers", *The Plant Journal*, 10, 165–174 (1996).

McCabe et al., "Stable Transformation of Soybean (*Glycine Max*) by Particle Acceleration", *Bio/Technology*, 6, 923–926 (1988).

Moloney et al., "Transformation and Foreign Gene Expression" in *Monographs Theoretical and Applied Genetics (19)*; Frankel et al., Eds.; Springer–Verlag: NY; pp. 148–167 (1993).

Morocz et al., "An improved system to obtain fertile regenerants via maize protoplasts isolated from a highly embroyogenic suspension culture", *Theor. Appl. Genet.*, 80, 721–726 (1990).

Neuffer, "Growing Maize for Genetic Purposes"; in *Maize for Biological Research;* Sheridan, Ed.; Plant Molecular Biology Assoc.; pp. 19–30 (1982).

Ohta et al., "Construction and Expression in Tobacco of a β–Glucuronidase (GUS) Reporter Gene Containing an Intron Within the Coding Sequence", *Plant Cell Physiol.*, 31, 805–813 (1990).

Potrykus, "Gene Transfer to Cereals: An Assessment", *BioTechnology*, 535–542 (1990).

Schafer et al., "T–DNA integration and expression in a monocot crop plant after induction of *Agrobacterium*", *Nature*, 327, 529–532 (1987).

Skirvin, "Fruit Crops" in Coning Agricultural Plants Via In Vitro Techniques; Conger, ed.; CRC Press: Boca Raton, FL; pp. 51–140 (1981).

Songstad et al., "Advances in alternative DNA delivery techniques", *Plant Cell, Tissue and Organ Culutre*, 40, 1–15 (1995).

Songstad et al., "Production of Transgenic Maize Plants and Progeny by Bombardment of Hi–II Immature Embryos", *In Vitro Cell, Dev. Biol.–Plant*, 32, 179–183 (1996).

Smith et al., "*Agrobacterium tumefaciens* Transformation of Monocotyledons", *Crop Sci.*, 35, 301–309 (1995).

Thompson et al., "Characterization of the herbicide–resistance gene bar from *Streptomyces hygroscopicus*", *EMBO J.*, 6, 2519–2523 (1987).

Vancanneyt et al., "Construction of an intron–containing marker gene: Splicing of the intron in transgenic plants and its use in monitoring early events in Agrobacterium–mediated plant transformation", *Mol. Gen. Genet.*, 220, 245–250 (1990).

West et al., "Embryogenesis in Higher Plants: An Overview", *The Plant Cell*, 5, 1361–1369 (1993).

Wilson et al., "Maize" in *Transformation of Plants and Soil Microorganisms;* Wang et al. eds.; Cambridge University Press, pp. 65–80 (1995).

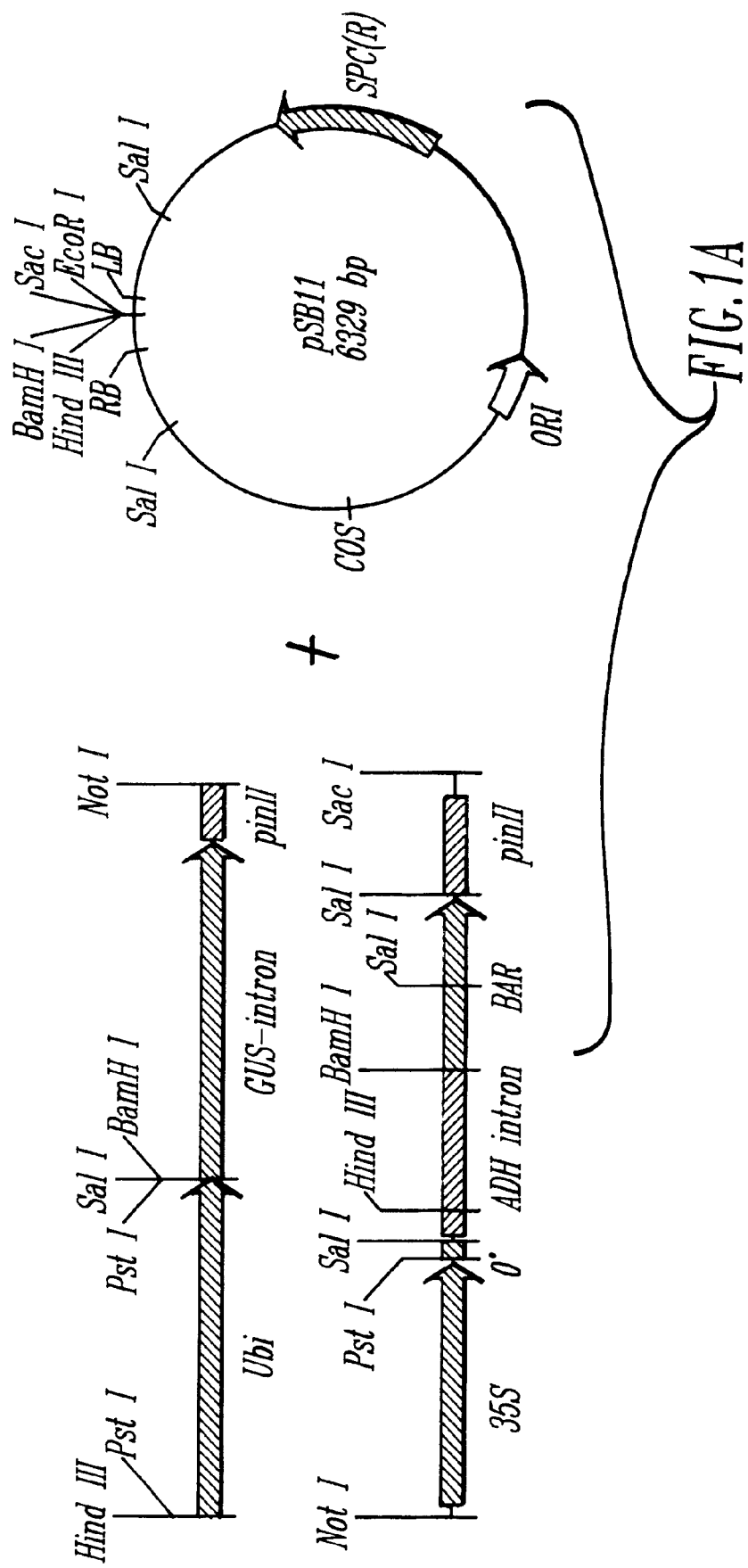

METHODS FOR AGROBACTERIUM-MEDIATED TRANSFORMATION

FIELD OF THE INVENTION

This invention relates to methods for plant tissue culture and plant regeneration and in particular this invention relates to methods for transforming maize using Agrobacterium.

BACKGROUND OF THE INVENTION

Agrobacterium-mediated transformation methods have been used principally in dicotyledonous plants. Agrobacterium-mediated transformation in dicotyledons facilitates the delivery of larger pieces of heterologous nucleic acid as compared with other transformation methods such as particle bombardment, electroporation, polyethylene glycol-mediated transformation methods, and the like. In addition, Agrobacterium-mediated transformation appears to result in relatively few gene rearrangements and more typically results in the integration of low numbers of gene copies into the plant chromosome.

Monocotyledons are not a natural host of Agrobacterium. Although Agrobacterium-mediated transformation has been reported for asparagus (Bytebier B., et al. *Proc. Natl. Acad. Sci. USA* 84:5354–5349, 1987) and for *Dioscore bublifera* (Schafer et al. *Nature* 327:529–532, 1987), it was generally believed that plants in the family Gramineae could not be transformed with Agrobacterium (Potrykus I. *Biotechnology* 8:535–543, 1990).

Grimsley et al. (*Nature* 325:177–179, 1987) reported that cDNA from maize streak virus could be delivered to maize plants by *Agrobacterium tumefaciens* and that the plants became infected with the virus. The research did not demonstrate that the cDNA reached the maize genome nor did it demonstrate stable integration of streak virus nucleic acid. Later studies demonstrated that Agrobacterium could be used to deliver a kanamycin-resistance gene and a GUS (β-glucuronidase) gene to shoot apices of maize after shoot apex injury (Gould J. et al. *Plant Physiol.* 95:426–434, 1991 and U.S. Pat. No. 5,177,010 to Goldman et al.). In these studies plants generated from the tissue exposed to Agrobacterium contained both transformed cells and non-transformed cells suggesting that the method did not uniformly deliver nucleic acid to the maize tissue.

European Patent Application Publication Number 604 662 A1 to Hiei et al. discloses a method for transforming monocotyledons using Agrobacterium. In this method, plant tissues were obtained from the monocotyledon maize and the tissues were exposed to Agrobacterium during the tissue dedifferentiation process. Hiei et al. disclose a maize transformation protocol using maize calli. Saito et al. disclose a method for transforming monocotyledons using the scutellum of immature embryos (European Application 672 752 A1). Ishida et al. also disclose a method specific for transforming maize by exposing immature embryos to *A. tumefaciens* (Nature Biotechnology, 1996, 14:745–750). The methods were optimized for inbred A188 maize lines. Transformation frequencies ranged from 12% to 30% at their highest for immature embryos from A188 lines that were 1.0–1.2 mm in length. Maize lines derived from crosses of A188 had significantly lower transformation frequencies ranging from 0.4% to about 5.3%. The transformation frequencies using A188 and A188 crosses are summarized in Table 1. A188 is not generally considered a commercially useful line and Ishida et al. failed to obtain recovery of stable transformants in lines other than those containing A188.

A need still exists for a method that will: (a) produce significantly higher transformation frequencies in lines other than those reported by Ishida et al. (supra); and, (b) produce transformed inbred lines other than line A188; including transformed inbreds representing a range of genetic diversities and having significant commercial utility.

SUMMARY OF THE INVENTION

This invention relates to methods for optimizing Agrobacterium-mediated transformation in maize. Significantly higher transformation frequencies for genotypes such as the product of A188 crossed to other inbreds would result in a higher throughput for production of transformed plants. This increased frequency would be useful, for example, to evaluate the efficacy of a larger number of genes in transgenic plants of corn or to generate a larger number of transgenic plants containing a particular foreign gene in a given period of time. Similarly, methods permitting the transformation of a variety of inbred lines would be commercially valuable.

In one aspect of this invention, the invention relates to a method for transforming maize using Agrobacterium comprising the steps of: contacting at least one immature embryo from a maize plant with Agrobacterium capable of transferring at least one gene to the embryo; co-cultivating the embryo with Agrobacterium; culturing the embryo in a medium comprising N6 salts, an antibiotic capable of inhibiting the growth of Agrobacterium, and a selective agent to select for embryos expressing the gene; and regenerating maize plants expressing the gene. In one embodiment the contacting step additionally comprises the step of contacting the immature embryos with Agrobacterium in a medium comprising N6 salts and in another embodiment the contacting step additionally comprises contacting the immature embryos with Agrobacterium in a medium comprising MS salts. Preferably the contacting step takes place in the absence of $AgNO_3$. In one embodiment the embryos are cultured in a PHI basic media system and in another embodiment the embryos are cultured in a PHI combined media system. The immature embryos used in the method are preferably about 0.3 mm to about 4 mm in length and more preferably about 0.8 mm to about 2.0 mm in length. The Agrobacterium concentration used in the contacting step is preferably about $1\times10^8$ cfu/ml to about $1.5\times10^9$ cfu/ml and more preferably about $0.5\times10^9$ to about $1.0\times10^9$ cfu/ml. The contacting step preferably takes place in a liquid suspension and the co-cultivation step preferably takes place on a solid medium. Preferably, a medium containing MS salts is used in the regeneration step. In a preferred embodiment of this invention the method includes a resting step that comprises culturing the embryos in medium containing an antibiotic capable of inhibiting the growth of Agrobacterium. Preferably the embryos are cultured for about 1 to about 15 days. In one embodiment the antibiotic used is carbenicillin and a preferred concentration of carbenicillin is about 50 mg/l to about 250 mg/l. This method also relates to maize plants transformed by this method and to maize cells transformed by this method.

In another aspect of this invention, the invention relates to a method for transforming maize using Agrobacterium comprising the steps of: contacting at least one immature embryo from a maize plant with Agrobacterium capable of transferring at least one gene to said embryo in a medium comprising N6 salts; co-cultivating the embryo with Agrobacterium in a medium comprising N6 salts; culturing the embryo in a medium comprising N6 salts, an antibiotic capable of inhibiting the growth of Agrobacterium, and a selective agent to select for embryos expressing the gene; and regenerating plants expressing the gene in a medium comprising MS salts. Preferably, the medium of the contacting step lacks AgNO$_3$ and the medium of the co-cultivating step includes AgNO$_3$. Preferably the Agrobacterium concentration used in the contacting step is about 1×10$^8$ cfu/ml to about 1.5×10$^9$ cfu/ml. Preferably, the contacting step takes place in a liquid and the co-cultivating and culturing steps take place on a solid medium. In one embodiment of this method, the method additionally comprising the step of resting the embryo by culturing the embryo in a medium containing an antibiotic capable of inhibiting the growth of Agrobacterium. Preferably the antibiotic is carbenicillin. This invention also relates to maize plants and to maize cells transformed by this method.

In yet another aspect of this invention, a method is disclosed for transforming maize using Agrobacterium comprising the steps of: contacting at least one immature embryo from a maize plant with Agrobacterium capable of one immature embryo from a maize plant with Agrobacterium capable of transferring at least one gene to said embryo in a medium comprising N6 or MS salts; co-cultivating the embryo with Agrobacterium in a medium comprising MS salts; culturing the embryo in a medium comprising N6 salts, an antibiotic capable of inhibiting the growth of Agrobacterium, and a selective agent to select for embryos expressing the gene; and regenerating plants expressing the gene in a medium comprising MS salts. Preferably the medium of the contacting step lacks AgNO$_3$ and the method of the co-cultivating step includes AgNO$_3$. Also preferably, the contacting step takes place in a liquid and the co-cultivating and culturing steps take place on a solid medium. In one embodiment of this method, the method additionally comprising the step of resting the embryo by culturing the embryo in a medium containing an antibiotic capable of inhibiting the growth of Agrobacterium.

This invention also relates to a method for optimizing the production of transgenic maize plants of a first genotype using Agrobacterium-mediated transformation comprising the steps of: isolating immature embryos from maize; separating the embryos into treatment groups; incubating each treatment group separately in a medium comprising N6 or MS salts and in a suspension of Agrobacterium at concentrations ranging from about 1×10$^8$ cfu/ml to about 1×10$^{10}$ cfu/ml; co-cultivating the embryos with Agrobacterium on a solid medium; culturing the embryos in a medium comprising N6 salts, an antibiotic capable of inhibiting the growth of Agrobacterium, and a selective agent to select for embryos transformed by Agrobacterium; identifying the treatment group with the highest transformation frequency; and using the concentration of Agrobacterium generating the highest transformation frequency to transform other embryos from the first genotype. In one embodiment of this method, the medium of the incubating step and the co-cultivating step is a medium comprising N6 salts and in another embodiment of this method, the medium of the incubating step is a medium comprising MS salts and the medium of the co-cultivating step is a medium comprising N6 salts. In yet another embodiment, medium of the incubating step is a medium comprising N6 salts and the medium of the co-cultivating step is a medium comprising MS salts. The method also preferably includes the step of resting the embryo by culturing the embryo in a medium containing an antibiotic capable of inhibiting the growth of Agrobacterium. Preferably the antibiotic is carbenicillin and preferably, the combined length of the co-cultivating step and the resting step is at least three days. Where a resting step is used, the length of the resting step is from more than 0 to about 10 days. In a preferred embodiment, the length of the resting step is about 3 to about 5 days.

In another aspect of this invention, the invention relates to transformed maize plants produced by a method comprising the steps of: contacting at least one immature embryo from a maize plant with Agrobacterium capable of transferring at least one gene to the embryo; co-cultivating the embryo with Agrobacterium; culturing the embryo in a medium comprising N6 salts, an antibiotic capable of inhibiting the growth of Agrobacterium, and a selective agent to select for embryos expressing the gene; and regenerating plants expressing the gene.

In yet another aspect of this invention, the invention relates to transformed maize cells produced by a method comprising the steps of: contacting at least one immature embryo from a maize plant with Agrobacterium capable of transferring at least one gene to the embryo; co-cultivating the embryo with Agrobacterium; and culturing the embryo in a medium comprising N6 salts, an antibiotic capable of inhibiting the growth of Agrobacterium, and a selective agent to select for embryos expressing the gene: and identifying embryos expressing the gene.

In a preferred aspect of this invention, the invention relates to a method for transforming maize using Agrobacterium comprising the steps of: contacting at least one immature embryo from a maize plant with Agrobacterium capable of transferring at least one gene to the embryo; co-cultivating the embryo with Agrobacterium; culturing the embryo in a medium containing salts other than MS salts, an antibiotic capable of inhibiting the growth of Agrobacterium, and a selective agent to select for embryos expressing the gene; and regenerating plants expressing the gene.

BRIEF DESCRIPTION OF THE FIGURES

FIG. 1 provides a diagram illustrating the construction of a preferred vector of this invention. FIG. 1(a) diagrams the exemplary gene segments incorporated into the exemplary vectors used in a preferred method of this invention.

DETAILED DESCRIPTION OF THE PREFERRED EMBODIMENTS

Figure 1B:
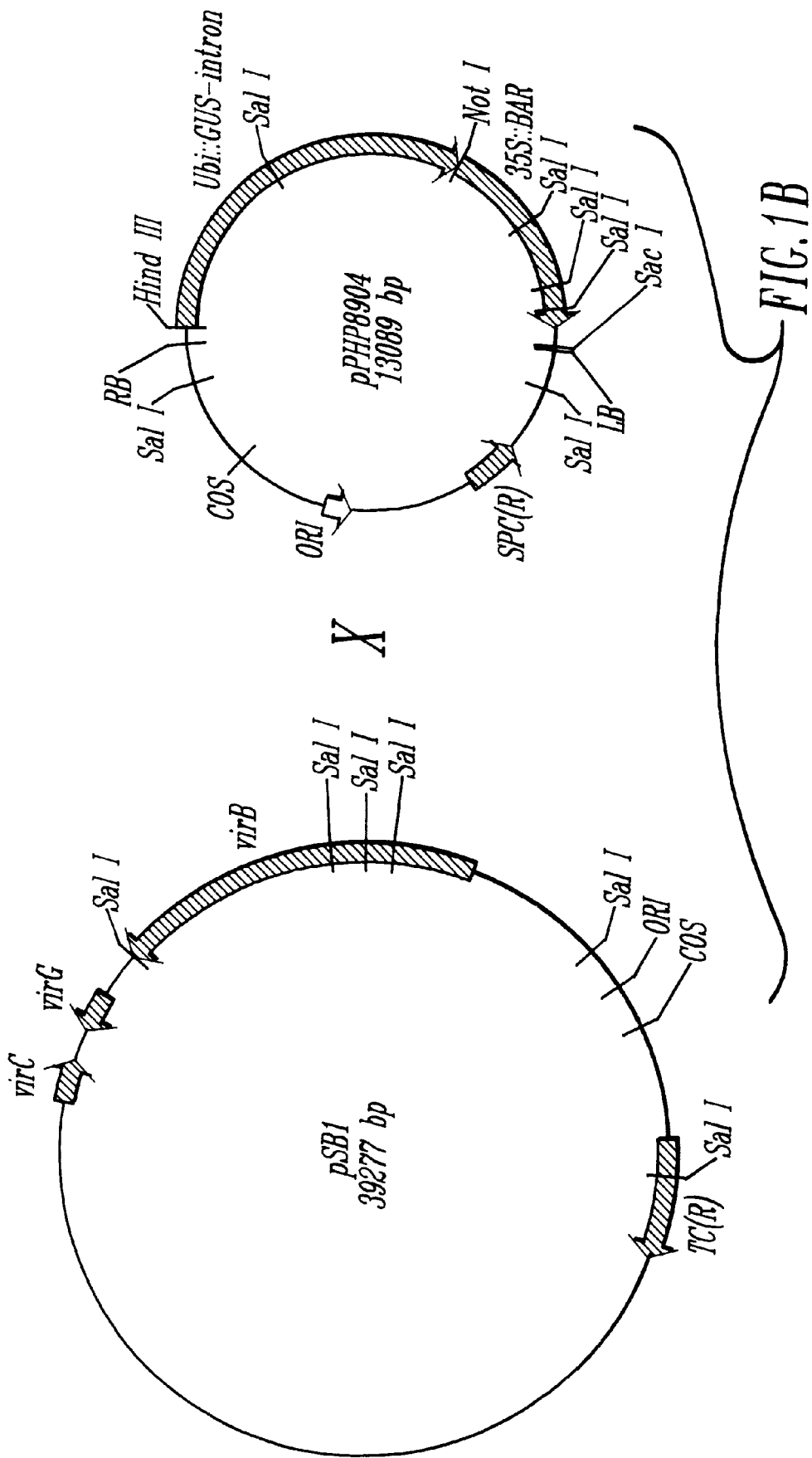
FIG. 1(b) illustrates plasmid pPHP8904 incorporating the exemplary gene segments.

The development of maize hybrids requires, in general, the development of homozygous inbred lines, the crossing of these lines, and the evaluation of the crosses. Pedigree breeding and recurrent selection breeding methods are used to develop inbred lines from breeding populations. Breeding programs combine the genetic backgrounds from two or more inbred lines or various other broad-based sources into breeding pools from which new inbreds are developed by selfing and selection of desired phenotypes. The new inbreds are crossed with the inbred lines and the hybrids from these crosses are evaluated to determine which of those have commercial potential.

Pedigree breeding starts with the crossing of two genotypes, each of which may have one or more desirable characteristics that is lacking in the other or which complements the other. If the two original parents do not provide all of the desired characteristics, other sources can be included in the breeding population. A single cross hybrid maize variety is the cross of two inbred lines, each of which has a genotype that complements the genotype of the other. The hybrid progeny of the first generation is designated F$_1$. In the development of hybrids, only the F$_1$ hybrid plants are sought. Preferred hybrids are more vigorous than their inbred parents. This hybrid vigor, or heterosis, can be maintained in many polygenic traits, including increased vegetative growth and increased yield.

The development of a hybrid maize variety involves three steps: (1) selection of plants from various germplasm pools for initial breeding crosses; (2) the selfing of the selected plants from the breeding crosses for several generations to produce a series of inbred lines, that, although different from each other, are highly uniform; and (3) crossing the selected inbred lines with different inbred lines to produce the hybrid progeny ($F_1$). Inbred lines produced in such a breeding program naturally fall into what are termed different heterotic groups. Maximal heterosis, or hybrid vigor, is typically produced by crossing two inbreds, each from a different heterotic group. At least several distinct heterotic groups can be identified, with numerous inbreds belonging to each heteotic group. A significant amount of research and development goes into the identification and recovery of inbred lines of commercial importance. For example, some 400–500 new inbred lines may be proposed by a single seed corn corporation each year as a result of over 2,000,000 pollinations. Of those proposed new inbreds, fewer than 50 and more commonly fewer than 30 are selected for commercial use. Those inbred lines that are used in commercially important hybrids are considered to be "elite" inbred lines. Not only is there a need to directly transform inbred lines that are commercially important for the hybrid corn market but there is also a need for those inbreds to cover a wide range of genetic diversity.

A188 is a useful genotype for the development of corn transformation methods, since it is known to be highly responsive in producing a friable type of embryogenic callus that lends itself to tissue culture (Phillips, R. L. et al. "Cell/Tissue Culture and In Vitro Manipulation" pp. 345–387, in *Corn and Corn Improvement*, G. F. Sprague and J. W. Dudley, eds., American Society of Agronomy, Inc., Crop Science Society of America, Inc., Soil Science Society of America, Inc. 1988 and Armstrong, C. L. et al., *Maize Genet. Coop. News Letter* 59:92–93, 1985). However, A188 is no longer generally considered to be a useful inbred parent of commercial hybrid corn. A188 is not used directly in any commercial hybrid and is a poor starting material for backcrossing into inbreds used as parents of commercial hybrids. Use of non-elite starting material for back crossing will in some cases delay release of the final commercial hybrid by one to two years. In addition, with non-elite starting material, there is a higher risk of negative genetic effects on the final hybrid product. Therefore, the ability to transform only A188-containing lines is of limited value to the commercial hybrid corn market.

Although Hiei et al. and Ishida et al., both supra, were successful in using Agrobacterium to transform A188-containing maize lines, non-A188 inbred lines could not be transformed using this method (Ishida et al. *Nature Biotechnology* 14:745–750, 1996). Some of the non-A188 inbreds tested included lines that were useful for hybrid field corn breeding. A significant need still exists for methods to transform non-A188 inbred lines, including inbred lines that are commercially important for the hybrid corn market. The commercial corn market includes a wide range of hybrids with different genetic backgrounds and successfull inbred breeding programs need to cover a wide range of genetic diversity.

High efficiency transformation of maize is important in analyzing the usefulness of any of a variety of genes in transgenic corn plants. High efficiency transformation of maize is also important because large numbers of transgenic plants are needed to study the effect of a particular gene within a given period of time. The ability to directly transform agronomically important inbreds at a usable frequency and across a wide range of genetic diversity is important for the development of commercial hybrid seed products with improved traits including, but not limited to, insect resistance, disease resistance, herbicide resistance, increased yield, increased tolerance to environmental stresses (such as drought, heat, etc.), enhanced seed quality (such as increased or modified starch, oil and/or protein content), and the like.

Although non-Agrobacterium-mediated transformation methods are known, including, but not limited to, particle bombardment, electroporation and silicon carbide fiber-mediated transformation (Songstad, D. D., et al. *Plant Cell, Tissue and Organ Culture* 40:1–15, 1995), the utility of these methods is limited because the methods produce low transformation frequencies and/or because the methods may only be useful for a restricted number of genotypes. For example, transformation frequencies by bombardment have been reported to be less than 2% for the "Hi-II" genotype used in the present invention (Songstad, D. D. et al. *In Vitro Cell. Dev. Biol. Plant* 32:179–183, 1996), even though Hi-II is one of the more responsive and efficient maize genotypes in tissue culture. Protoplast systems have also been used for transformation studies including electroporation and polyethylene glycol (PEG)-mediated methods for nucleic acid uptake. Reports indicate that maize protoplast systems can show good transformation frequencies (Donn, G., in *Abstracts of the VIIth International Congress on Plant Cell and Tissue Culture*, IAPTC, A2–38, p. 53, 1990). The protoplast genotype used in this study was a specially derived complex synthetic maize genotype, He/89, that demonstrated good regeneration capability and had low rate of plant abnormalities (Morocz, S., et al. *Theoretical and Applied Genetics* 80:721–726, 1990). However, aside from the specialty lines such as HE89, most genotypes, including agronomically important genotypes are not very amenable to the use of protoplast targeted transformation methods. Consequently, Wilson et al. (in *Transformation of Plants and Soil Microorganisms*, Wang, Herrera-Estrella et al. eds. Cambridge University Press, p. 65–80, 1995) conclude that "genotype constraints and the reduced vigor and fertility of plants regenerated from protoplasts probably outweigh the benefits of protoplasts as recipients for the integration of foreign DNA." Only a limited number of genotypes are amenable to the use of protoplasts for transformation and the quality of the plant produced from protoplast culture is often not as good as the quality of the plant produced from other transformation systems.

Ishida et al. (supra) discuss a method for transforming inbred A188 embryos and $F_1$ embryos derived from crosses of A188 with other inbred lines through the co-cultivation of the embryos with *Agrobacterium tumefaciens* using superbinary vectors. Table 1 of that publication summarized the frequencies for maize transformation obtained in that study. Maximum transformation frequencies reached 30.6% for A188 but the transformation frequency only reached 5.3% for embryos derived from crosses of A188 and the average transformation frequency for A188 was about 15%. Non-A188-containing lines could not be transformed by these methods. The transformation frequencies using embryos derived from A188 and $F_1$ embryos from crosses of A188, as reported in Table 1 of the Ishida et al paper, are summarized in Table 1 below. The transformation frequencies of $F_1$ embryos ranged from 0.4–5.3% and was defined as the proportion of total embryos which produced GUS expressing (GUS+) plants. In this table, and as used herein, the term "GUS+" refers to transgenic events where GUS gene expression can be detected.

TABLE 1

Transformation of A188 and crosses by Ishida et al.
The results in this Table were reported in Ishida et al., (Nature Biotechnology 14:745–750, 1996). GUS+ plants are those which showed positive staining for expression of the GUS gene.

| | | Number of immature embryos | | | | |
|---|---|---|---|---|---|---|
| Variety | Experiment No. | Inoculated (A) | Callus growing on herbicide | Plants regenerated on herbicide | GUS+ plants (B) | Frequency B/A$_1$ %) |
| A188 | 1 | 44 | 28 | 9 | 6 | 13.6 |
| | 2 | 52 | 33 | 10 | 7 | 13.5 |
| | 3 | 51 | 46 | 13 | 7 | 13.7 |
| | 4 | 70 | 56 | 26 | 14 | 20.0 |
| | 5 | 76 | 30 | 12 | 9 | 11.8 |
| | 6 | 369 | 200 | 71 | 44 | 11.9 |
| | 7 | 121 | 46 | 33 | 20 | 16.5 |
| | 8 | 27 | 15 | 8 | 5 | 18.5 |
| | 9 | 36 | 26 | 18 | 11 | 30.6 |
| | 10 | 77 | 38 | 32 | 16 | 20.8 |
| W117 × A188 | 1 | 112 | 36 | 8 | 4 | 3.6 |
| | 2 | 114 | 26 | 10 | 6 | 5.3 |
| W59E × A188 | 1 | 104 | 44 | 1 | 1 | 1.0 |
| A554 × A188 | 1 | 247 | 46 | 7 | 5 | 2.0 |
| W153R × A188 | 1 | 284 | 69 | 2 | 1 | 0.4 |
| H99 × A188 | 1 | 219 | 18 | 4 | 3 | 1.4 |

The present invention, while complementing the work of Ishida et al., provides an improved method for generating a significant increase in Agrobacterium-mediated transformation frequency for A188-containing lines and for successfully transforming non-A188 inbreds across a wide range of genotypes. In this invention, methods described by Ishida et al. (including the same source of A188 and the same vector) were used to transform A188 lines to demonstrate that the Ishida et al. methods could be reproduced in a different laboratory, on the same A188 genotype. The results of these initial transformation studies are provided in Example 2 and the data are summarized in Table 3. The results of these experiments produced transformation frequencies similar to those reported by Ishida et al. and ranged from about 9% to about 18% for A188 transformation in four separate experiments.

The methods of Ishida et al. were then used to transform a genotype termed Hi-II. This provided a baseline for transformation frequencies that could be used as a comparison with the transformation protocols of this invention. Hi-II is similar to the A188×inbred crosses used by Ishida et al. (i.e., those listed in Table 1) to the extent that Hi-II is derived from both A188 and a non-A188 inbred, B73 (Armstrong et al. *Maize Genetics Cooperation Newsletter* 65:92–93, 1991). Details on the derivation of Hi-II and the results of the Hi-II transformation studies using the Ishida et al. method, are provided in Example 3. The data are summarized in Table 4. The results of these experiments show that transformation frequencies obtained for Hi-II, using the protocols of Ishida et al., ranged from 0.8 to 7.1% and were also in the same general range of transformation frequencies as those obtained by Ishida et al. for A188 inbred crosses. The results reported in Example 2 and Example 3 demonstrated that the method of Ishida et al. was reproducible by others. These results allow comparisons to be made between the new Agrobacterium-mediated transformation methods of this invention and those reported in the literature.

The preferred Agrobacterium-mediated transformation process of this invention differs from that of Ishida et al. and Hiei et al. in several respects and can be broken into several steps.

As will be discussed in more detail below, immature embryos are isolated from maize and the embryos contacted with a suspension of Agrobacterium (step 1; the infection step). In this step the immature embryos are preferably immersed in an Agrobacterium suspension for the initiation of inoculation. The embryos are co-cultured for a time with the Agrobacterium (step 2; the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4; the selection step). Preferably, the immature embryos are cultured on solid medium with a selective agent resulting in the selective growth of transformed cells. The callus is then regenerated into plants (step 5; the regeneration step) and preferably calli grown on selective medium are cultured on solid medium to regenerate the plants.

Infection Step

As a first step for practicing this invention, immature embryos are isolated from maize and exposed to Agrobacterium. Immature embryos are an intact tissue that is capable of cell division to give rise to callus cells that can then differentiate to produce tissues and organs of a whole plant. Immature embryos can be obtained from the fertilized reproductive organs of a mature maize plant. Exemplary methods for isolating immature embryos from maize are described by Green and Phillips (*Crop Sci.* 15:417–421, 1976). Maize immature embryos can be isolated from pollinated plants, as another example, using the methods of Neuffer et al. ("Growing Maize for genetic purposes." In: *Maize for Biological Research* W. F. Sheridan, Ed., University Press, University of North Dakota, Grand Forks, N.

Dak. 1982.). Another method is provided in Example 4. The immature embryos are preferably used at approximately 6 days to about 20 days after pollination, more preferably about 7 days to 18 days after pollination, still more preferably about 8 days to 16 days after pollination, and in a particularly preferred embodiment about 9 days to about 12 days after pollination. Preferably, the embryos exposed to Agrobacterium range from about 0.3 to 4 mm in size, more preferably about 0.6 to 3.0 mm, still more preferably about 0.8 to 2.0 mm and in a particularly preferred embodiment about 1.0 mm to about 1.2 mm in size. Immature embryos are preferably aseptically isolated from the developing ear and held in sterile medium until use.

The Agrobacterium used to transform the embryos is modified to contain a gene of interest. Preferably the gene is incorporated into a gene vector, to be delivered to the embryo. A variety of Agrobacterium species are known and Agrobacterium species employed for dicotyledon transformation can be used. A number of references review Agrobacterium-mediated transformation in monocots and dicots. These include, among others, Hooykaas, P. J. (*Plant Mol Biol.*, 13:327–336, 1989); Smith, R. H. et al. (*Crop Science*, 35:301–309, 1995); Chilton, M. O. (*Proc. Natl. Acad. Sci.* (USA), 90:3119–3210, 1993); and Moloney et al. In: *Monograph Theor. Appl. Genet.*, NY, Springer Verlag 19:148–167, 1993).

Many Agrobacterium employed for the transformation of dicotyledonous plant cells contain a vector having a DNA region originating from the virulence (vir) region of the Ti plasmid. The Ti plasmid originated from *Agrobacterium tumefaciens*. Nucleic acid containing a gene encoding a polypeptide to be expressed in maize can be inserted into this vector. Alternatively, the gene can be contained in a separate plasmid which is then inserted into the Ti plasmid in vivo, in Agrobacterium, by homologous recombination or other equivalently resulting processes. A vector has also been developed which contains a DNA region originating from the virulence (vir) region of Ti plasmid pTiBo542 (Jin et al., 1987, *J. Bacteriol.* 169:4417–4425) contained in a super-virulent *Agrobacterium tumefaciens* strain A281 showing extremely high transformation efficiency. The plasmid containing the gene of interest was incorporated into the virulent *Agrobacterium tumefaciens* strain A281 since strain A281 is known to have a high transformation efficiency (see Hood, E. E. et al.,1984, *Bio/Tech* 2:702–709; Komari, T. et al., 1986, *Bacteriol* 166:88–94). This type of vector is known in the art as a "superbinary vector" (see European Patent Application 0 604662A1 to Hiei et al.).

Superbinary vectors are preferred vectors for the transformation methods of this invention. Exemplary superbinary vectors useful for introducing nucleic acid encoding polypeptide for expression in a maize plant via Agrobacterium-mediated transformation methods include the superbinary pTOK162 (as disclosed in Japanese Laid-Open Patent Application no. 4-222527). This vector includes regions that permit vector replication in both *E. coli* and *A. tumefaciens*. The plasmid includes a T-DNA region, characteristic of Ti plasmids. Nucleic acid containing a gene encoding a polypeptide to be expressed in maize is inserted in the T-DNA between the T-DNA borders. Other superbinary vectors are known and these vectors can similarly be incorporated into Agrobacterium (see e.g., Komari, T., *Plant Cell Reports* 9:303–306, 1990 for pTOK23).

Examples of genes useful for expression in transformed plant cells are known in the art. Exemplary genes include, but are not limited to, Bt genes or patatin genes for insect resistance; the Hm1 gene and chitinase genes for disease resistance; the pat, bar, EPSP syntase gene or ALS genes for herbicide resistance; genes encoding proteins with altered nutritional properties; genes encoding enzymes involved in starch or oil biosynthetic pathways; down-or up-regulatory sequences for metabolic pathway enzymes; and the like. As those of ordinary skill in the art will recognize, this is only a partial list of possible genes that can be used with the transformation method of the present invention. Furthermore, as those of ordinary skill in the art will also recognize, regulatory sequences including promoters, terminators and the like will also be required, and these are generally known in the art. Example 1 discloses the construction of a preferred superbinary vector pPHP10525. This vector contains virB, virC and virG genes isolated from superviral strain A281. The vector includes 35Sbar and ubi/GUS plant expression cassettes inserted between the T-DNA borders. Plant expression cassettes preferably comprise a structural gene to which is attached regulatory DNA regions that permit expression of the gene in plant cells. The regulatory regions consist at a minimum of a promoter capable of directing expression of a gene in a plant cell. The promoter is positioned upstream or at the 5' end of the gene to be expressed. A terminator is also provided as a regulatory region in the plant expression cassette and is capable of providing polyadenylation and transcription terminator functions in plant cells. The terminator is attached downstream or at the 3' end of the gene to be expressed. Marker genes, included in the vector, are useful for assessing transformation frequencies in this invention.

The nucleic acid encoding a polypeptide for expression in maize is inserted into the T-DNA region of the superbinary vector using suitable restriction endonuclease recognition sites, by homologous recombination, or the like. General molecular biological techniques used in this invention are provided, for example, by Sambrook, et al. (eds.) (*Molecular Cloning: A Laboratory Manual,* 1989, Cold Spring Harbor Laboratory Press, Cold Spring Harbor, N.Y.) and the use of homologous recombination to incorporate nucleic acid into plasmids contained in *Agrobacterium tumefaciens* is disclosed by Herrera-Esterella, L. et al. (*EMBO J.* 2:987–995, 1983) and Horsch R. H. et al., (*Science* 223:496–498, 1984). The recombinant plasmid is selected in Agrobacterium based on the use of a selectable marker incorporated into the plasmid. Generally these markers are nucleic acid encoding proteins that typically confer antibiotic resistance.

Plasmids are introduced into Agrobacterium using methods known in the art, including the triple-cross method disclosed by Ishida et al. (supra) and in a preferred embodiment the plasmid is introduced into Agrobacterium using the method of Example 1.

Agrobacterium containing the plasmid of interest are preferably maintained on Agrobacterium master plates with stock frozen at about −80° C. As used in this invention the term "Agrobacterium capable of transferring at least one gene" refers to Agrobacterium containing the gene of interest, generally in a plasmid that is suitable for mediating the events required to transfer the gene to the cells to be infected. In a preferred embodiment, the master plates are used to inoculate agar plates to obtain Agrobacterium which is then resuspended in media for use in the infection process as described in Example 2. Alternatively, bacteria from the master plate can be used to inoculate broth cultures that are grown to logarithimic phase prior to transformation.

The concentration of Agrobacterium used in the infection step and co-cultivation step can affect the transformation frequency. For example, while Agrobacterium can transform immature embryos of maize, very high concentrations of Agrobacterium may also damage the immature embryos and result in a reduced callus response. To optimize the transformation protocol for a particular maize line, immature embryos from the maize line can be incubated with various concentrations of Agrobacterium. Using the protocols provided in Examples 2–6, the level of marker gene expression and the transformation efficiency can be assessed for various Agrobacterium concentrations preferably within the concentration range of about $1.0 \times 10^8$ cfu/ml to about $1 \times 10^{10}$ cfu/ml. Table 6 in Example 4 demonstrated the effect of varying Agrobacterium concentration to optimize the Agrobacterium concentration for transformation. Using these methods, and those known in the art, concentrations of Agrobacterium in the infection and co-cultivation step that maximize the transformation frequency for a particular maize line can be identified without undue experimentation.

Preferably, Agrobacterium is used for transformations in a concentration range of about $1 \times 10^8$ cfu/ml to about $1 \times 10^{10}$ cfu/ml, more preferably within the range of about $1 \times 10^8$ cfu/ml to about $1.5 \times 10^9$ cfu/ml and still more preferably at about $0.5 \times 10^9$ cfu/ml to about $1.0 \times 10^9$ cfu/ml. Those skilled in the art will recognize that optimum Agrobacterium concentration ranges may vary for particular maize genotypes and for the particular Agrobacterium strain.

The isolated embryos are added to the Agrobacterium suspension in a liquid contact phase. Preferably the Agrobacterium concentration is selected based on methods disclosed herein to optimize transformation efficiencies. Example 4 provides a preferred method for contacting the embryos with Agrobacterium in a liquid. The contact phase facilitates maximum contact of the immature embryos with the suspension of Agrobacterium. Preferably the embryos are contacted with the suspension of Agrobacterium for a period of at least 5 minutes and preferably between 5 to 15 minutes and more preferably for about 10 minutes.

Preferably the liquid contact phase of the infection step takes place in a liquid solution that includes the major inorganic salts and vitamins of N6 medium referred to herein as "N6 salts" (Chu C. C. *Proc. Symp. Plant Tissue Culture*, Science Press Peking. pp. 43–50, 1987). As used herein, medium containing "N6 salts" includes medium containing about 400–500 mg/l ammonium sulfate and preferably about 463.0 mg/l ammonium sulfate; about 1.0–2.0 mg/l boric acid and preferably about 1.6 mg/l boric acid; about 100–140 mg/l calcium chloride anhydrous and preferably about 125 mg/l calcium chloride anhydrous; about 20–50 mg/l $Na_2$-EDTA and preferably about 37.25 mg/l $Na_2$-EDTA; about 20–40 mg/l ferrous sulfate.$7H_2O$ and preferably about 27.8 mg/l ferrous sulfate.$7H_2O$; about 80–100 mg/l magnesium sulfate and preferably about 90.37 mg/l magnesium sulfate.$H_2O$, about 1.5–7 mg/l manganese sulfate.$H_2O$ and preferably about 3.33 mg/l manganese sulfate; about 0.4–1.6 mg/l potassium iodide and preferably about 0.8 mg/l potassium iodide; about 1,500–3,500 mg/l potassium nitrate and preferably about 2,830 mg/l potassium nitrate; about 200–600 mg/l potassium phosphate monobasic and preferably about 400 mg/l potassium phosphate monobasic; and, about 1.0–2.5 mg/l zinc sulfate.$7H_2O$ and preferably about 1.25–1.75 mg/l zinc sulfate.$7H_2O$. Other equivalent liquid suspensions can be used and, as summarized in Table 2, media containing MS salts was also successfully used in the infection step. MS salts include about 1,650.0 mg/l ammonium nitrate, about 6.2 mg/l boric acid, about 332.2 mg/l calcium chloride anhydrous, about 0.025 mg/l cobalt chloride.$6H_2O$, about 0.025 mg/l cupric sulfate.$5H_2O$, about 37.26 mg/l $Na_2$-EDTA, about 27.8 mg/l ferrous sulfate.$7H_2O$, about 180.7 mg/l magnesium sulfate.$H_2O$, about 16.9 mg/l manganese sulfate.$H_2O$, about 0.83 mg/l potassium iodide, about 1,900.0 mg/l potassium nitrate, about 170.0 mg/l potassium phosphate monobasic, and about 8.6 mg/l zinc sulfate.$7H_2O$. Three different media, PHI-A, PHI-G and PHI-I, were tested in the infection step and these formulations are provided in the Examples.

Preferred media used in this step is provided in Example 4. In addition, the media in the infection step preferably excludes $AgNO_3$. $AgNO_3$ is preferably included in the co-cultivation, resting (when used) and selection steps when N6 media is used.

Those skilled in the art will recognize that although this method is disclosed for embryos isolated from maize, the method can also be used to transform maize cell suspensions. Therefore, the term "plant cells" as used in this invention can refer to isolated maize cells, including suspension cultures as will as to cells in an intact tissue, such as maize embryos.

Co-cultivation Step

In a next step of a preferred transformation protocol of this invention, the immature embryos are co-cultivated with the Agrobacterium on a solid medium. The embryos are preferably positioned axis down on the solid medium and the medium preferably includes $AgNO_3$ at a range of about 0.85 to 8.5 mg/l, although 0.01 to 200 mg/l can also be used. The embryos are preferably co-cultivated with the Agrobacterium for about 1–30 days, preferably about 2–20 days and more preferably about 3–10 days.

Two media regimes have been identified as useful in the methods of this invention: PHI basic medium and PHI combined medium. A summary of the media regimes used is provided in Table 2. The PHI basic medium contains N6 salts and is used in one embodiment of this invention, in the infection, co-cultivation optional resting and selection steps of this invention; MS salts are preferably used in the regeneration step. The PHI combined medium contains either N6 or MS salts in the infection step, MS salts in the co-cultivation step, N6 salts in the optional resting step and in the selection step and preferably MS salts in the plant regeneration step (Table 2). As illustrated in Examples 4–6, both basic media, containing N6 salts (for example, PHI-B), and the combined medium, using MS salts (for example, PHI-J), in the co-cultivation step demonstrated improved transformation efficiencies.

Preferably, where embryos are incubated on solid media containing N6 salts, the embryos remain on media containing N6 salts through the selection step. For embryos incubated in the co-cultivation step on MS containing medium, the embryos are preferably incubated in N6 salt-containing medium for the optional resting and the selection step. The preferred media combinations of this invention are summarized in Table 2.

Although Saito et al. and Hiei et al. cite the use of N6 salts for rice, Saito et al. specifically cite the use of LS salts rather than N6 salts in the examples for maize. Ishida et al. tested both LS and N6 salts for maize, but failed to obtain any stable transformants with N6 salts. Ishida et al. considered LS salts to be "superior to N6-based media" (supra) and used LS salts for every step of the process in all further experiments. Therefore, whenever the protocol of Ishida et al. is cited in the present application, it is understood that LS salts are included in that protocol. The macro and micro salts in MS medium are identical to the macro and micro salts in LS medium, but the two media differ in the composition of some of the vitamins and other components (Skirvin R. M., In: *Cloning Agricultural Plants Via In Vitro Techniques*, B. V. Conger, ed., CRC Press, Knoxville, Tenn., pp. 51–140, 1981).

Optional Resting Step

Following the co-cultivation step, the embryos are optionally transferred to a second plate of solid medium containing an antibiotic capable of inhibiting the growth of Agrobacterium. This resting phase is performed in the absence of any selective pressures to permit preferential initiation and growth of callus from embryos containing the heterologous nucleic acid. Preferably, the antibiotic used to inhibit Agrobacterium is carbenicillin and the preferred concentrations of carbenicillin are about 50 mg/l to about 250 mg/l carbenicillin in the solid media, more preferably about 100–125 mg/l carbenicillin. A particularly preferred concentration of carbenicillin is about 100 mg/I. Other antibiotics can be used that inhibit the growth of Agrobacterium and these include for example Cefotaxime, timetin, vancomycin, and the like. Those of ordinary skill in the art of monocot transformation will recognize that the concentration of antibiotic can be optimized for a particular transformation protocol without undue experimentation. The resting phase cultures are preferably allowed to rest in the dark at 28° C. for about 3 to about 5 days, but about 1 to about 15 days can also be used. Example 4 uses a 3–5 day resting period. A preferred resting step medium is PHI-C as provided in the examples. In addition, although Hiei et al. and Saito et al. describe use of a "resting" step for rice, no such resting step is cited for maize nor used in the Ishida et al. protocol for maize.

Example 5 provides a comparison of the surprising benefits achieved using a resting step for maize line Hi-II. In a preferred embodiment of this invention, a resting step is provided; however, a resting step is not always required and where no resting step is used, an extended co-cultivation step may be added to provide a period of culture time prior to the addition of a selective agent (see Example 7).

Selection Step

Following the co-cultivation step, or following the resting step, where it is used, the embryos are exposed to selective pressure to select for those cells that have received and are expressing polypeptide from the heterologous nucleic acid introduced by Agrobacterium. In the selection step, the embryos are transferred to plates with solid medium that includes both an antibiotic to inhibit growth of the Agrobacterium and a selective agent. The agent used to select for transformants will select for preferential growth of explants containing at least one selectable marker insert positioned within the superbinary vector and delivered by the Agrobacterium. Example 1 incorporates the bar gene into a superbinary vector that is introduced into the Agrobacterium. The bar gene confers herbicide resistance to glufosinate-type herbicides, such as phosphinothricin (PPT) or bialaphos, and the like. Bialaphos was used to select for embryos that received and expressed the bar gene in Examples 2–6. Examples of other selective markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hml gene for resistance to the Hc-toxin, and other selective agents used routinely and known to one of ordinary skill in the art.

Preferably, media containing salts other than MS salts is used in the selection step and in a preferred embodiment, media containing N6 salts is used in the selection step. Exemplary medias used in the selection step include PHI-D and PHI-H, as provided in the examples. During selection, the embryos are cultured until callus formation is observed. Typically, calli grown on selection medium are allowed to grow to a size of about 1.5 to 2 cm. diameter.

Plant Regeneration Step

After the calli have reached the appropriate size, the calli are cultured on regeneration medium in the dark for about 1 to 3 weeks to allow the somatic embryos to mature. Preferred regeneration media included media containing MS salts, such as PHI-E and PHI-F media as provided in the Examples. The calli are then cultured on rooting medium in a light/dark cycle until shoots and roots develop. Methods for plant regeneration are known in the art and preferred methods are provided by Kamo et al. (1985, *Bot. Gaz.* 146(3):327–334), West et al. (1993, *The Plant Cell* 5:1361–1369), and Duncan et al. (1985, *Planta,* 165:322–332).

Small plantlets are then transferred to tubes containing rooting medium and allowed to grow and develop more roots for approximately another week. The plants are then transplanted to soil mixture in pots in the greenhouse.

The following table (Table 2) summarizes the preferred protocols of this invention.

TABLE 2

Summary of the steps, salts and antibiotic in PHI protocols for Agrobacterium-mediated maize transformation.

| | Transformation steps | | | | |
|---|---|---|---|---|---|
| Protocol | Step 1 | Step 2 | Step 3 | Step 4 | Step 5 |
| | Infection | Co-cultivation | Resting | Selection | Regeneration |
| Ishida et al. | LS | LS | None disclosed | LS cefotaxime | LS cefotaxime |
| PHI Basic | N6 | N6 | N6 carbenicillin | N6 carbenicillin | MS carbenicillin |
| PHI combined | MS or N6 | MS | N6 carbenicillin | N6 carbenicillin | MS carbenicillin |

The methods of this invention were applied to the maize line Hi-II. These results are provided in Example 4 and the data summarized in Table 5. The results of these experiments demonstrated that the methods of this invention do provide an increased transformation frequency for Hi-II as compared with the Ishida et al. protocol (Example 3 and Table 4). Plant regeneration frequency from stably-transformed callus in Hi-II and in other genotypes ranged from about 95% to about 100%, demonstrating that either GUS+ callus or GUS+ plants can be used as an indicator of transformation frequency. In Tables 4–8, GUS+ events represent either GUS+ callus or GUS+ plants. Therefore, in Table 4 and all subsequent tables, transformation frequency was calculated by dividing the number of embryos producing GUS+ events (either GUS+ callus or GUS+ plants) by the total number of embryos inoculated with Agrobacterium.

The methods of this invention were next applied to $F_1$ embryos of crosses between A188 and other inbred lines. The results of these transformation studies are provided in Example 6 and the data are summarized in Table 8. These results indicate that the methods of this invention produced an improved transformation frequency for crosses of A188 to the inbreds with transformation frequencies ranging from 6.9% to 47.7%. These transformation frequencies were significantly higher than the frequencies reported by Ishida et al. for A188×inbred crosses which ranged from 0.4 to 5.3%. Taking the results in Table 4 (using the Ishida et al. method) together with the results in Table 8, the methods of this invention provide for significantly improved transformation frequencies for A188-containing lines.

The present invention also provides an improved method for the transformation of a variety of inbred lines other than A188, and importantly including maize lines across a wide range of genetic diversity. Three different elite inbred lines were tested, belonging to three different heterotic groups and therefore representing a broad range of genetic diversity. The method of Ishida et al. was also tested on these same three inbreds, for comparison, using 594,644 and 263 embryos for lines PHJ90, PHN46 and PHP38, respectively. The results are provided in Example 7 and the data summarized in Table 9. These experiments demonstrated that the methods of this invention are successful in transforming inbred lines covering a wide genetic range. In contrast, no stable transformants were recovered in any of the three inbred lines using the methods of Ishida, et al. (supra) or those of Hiei et al. (European Patent Application Publication Number 604 662 A1). These results are significant because this data indicates that a variety of maize lines can be efficiently and consistently transformed.

The methods of this invention proved useful for a variety of maize lines. The data indicated that the methods of this invention provide substantial improvements in Agrobacterium-mediated transformation frequencies as compared to methods currently available in the art.

All references and publications cited herein are expressly incorporated by reference into this disclosure. Particular embodiments of this invention will be discussed in detail and reference has been made to possible variations within the scope of this invention. There are a variety of alternative techniques and procedures available to those of skill in the art which would similarly permit one to successfully perform the intended invention that do not detract from the spirit and scope of this invention.

EXAMPLE 1

Construction of Agrobacterium Vectors and Strains

All vectors were constructed using standard molecular biology techniques (Sambrook et al., (eds.), Supra). A reporter gene and a selectable marker gene for gene expression and selection was inserted between the T-DNA borders of a superbinary vector. The reporter gene included the β-glucuronidase (GUS) gene (Jefferson, R. A. et al., 1986, *Proc. Natl. Acad Sci. (USA)* 83:8447–8451) into whose coding region was inserted the second intron from the potato ST-LS1 gene (Vancanneyt et al., *Mol. Gen. Genet.* 220:245–250, 1990), to produce intron-GUS, in order to prevent expression of the gene in Agrobacterium (see Ohta, S. et al., 1990, *Plant Cell Physiol.* 31(6):805–813). Referring to FIG. 1(*a*), the 2 kb fragment of the promoter region of the maize ubiquitin gene Ubi-1 (Christensen et al., *Plant Mol. Biol.* 18:675–689, 1992), with added 5' HindIII and 3' BamHI restriction sites, was ligated to the 5' BamHI site of the GUS gene. A fragment containing bases 2 to 310 from the terminator of the potato proteinase inhibitor (pinII) gene (An et al., *Plant Cell* 1:115–122, 1989) was blunt-end ligated downstream of the GUS coding sequence, to create the GUS expression cassette. The 3' end of the terminator carried a NotI restriction site.

For the selectable marker, a Cauliflower Mosaic Virus 35S promoter with a duplicated enhancer region (2×35S; bases −421 to −90 and −421 to +2 from Gardner et al., *Nucl. Acids Res.* 9:2871–2888, 1981) with a flanking 5' NotI site and a 3' PstI site was created. A PstI/SalI fragment containing the 79 bp Tobacco Mosaic Virus leader (Gallie et al., *Nuc. Acids Res.* 15:3257–3273, 1987) was inserted downstream of the promoter followed by a SalI/BamHI fragment containing the first intron of the maize alcohol dehydrognease gene ADH1-S (Dennis et al., *Nuc. Acids Res.* 12:3983–3990, 1984). The BAR coding sequence (Thompson et al., *EMBO J* 6:2519–2523, 1987) was cloned into the BamHI site, with the pinII terminator ligated downstream, to create the BAR expression cassette. The pinII terminator was flanked by a 3' SacI site.

Figure 1C:
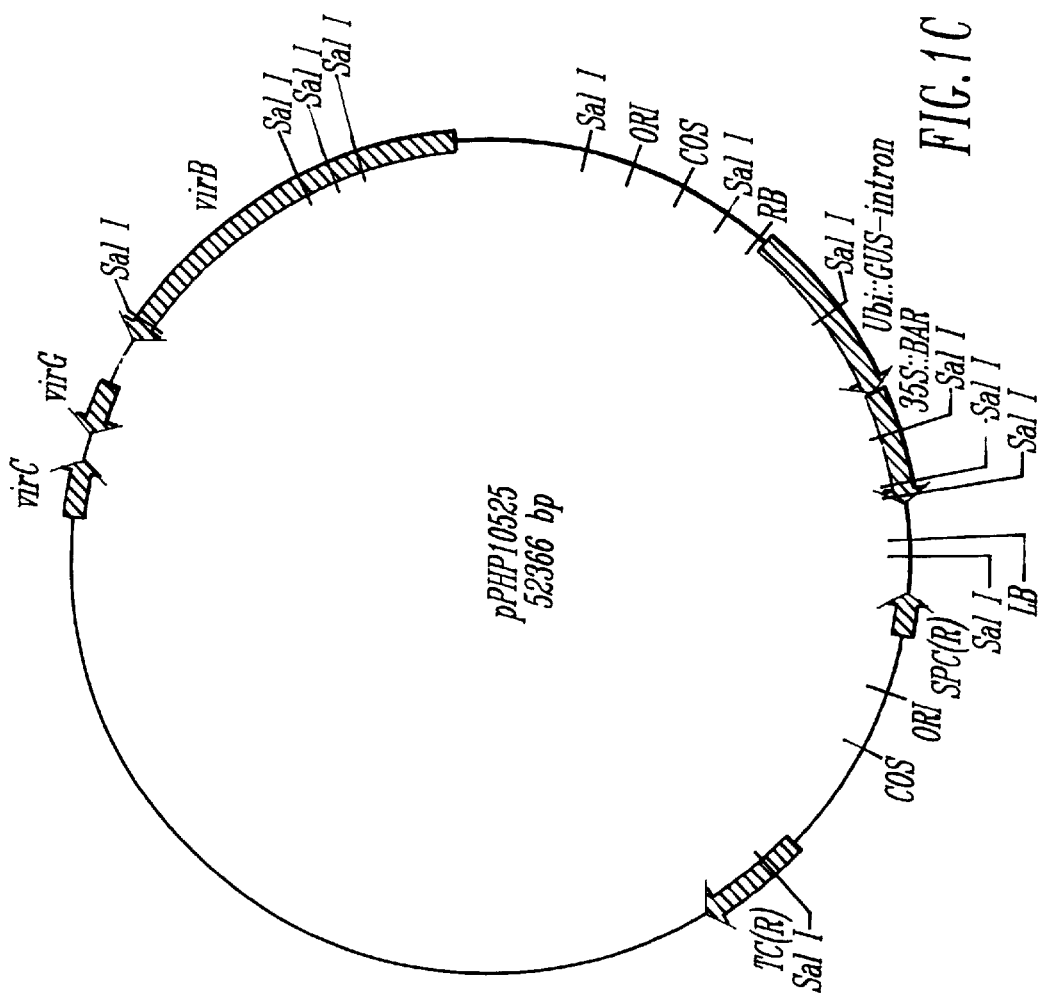
FIG. 1(c) illustrates plasmid pPHP 10525.

The plasmid, pPHP8904, (FIG. 1*b*) was constructed by inserting the GUS expression cassette as a HindIII|NotI fragment and the BAR expression cassette as a NotI/SacI fragment between the right and left T-DNA borders in pSB 11 at HindIII and SacI sites. The GUS cassette is inserted proximal to the right T-DNA border. The plasmid pSB11 was obtained from Japan Tobacco Inc. (Tokyo, Japan). The construction of pSB11 from pSB21 and the construction of pSB21 from starting vectors is described by Komari et al. (1996, Plant J. 10:165–174). The T-DNA of pPHP8904 was integrated into the superbinary plasmid pSB1 (Saito et al., EP 672 752 A1) by homologous recombination between the two plasmids (FIG. 1, pSB1×pPHP8904). The plasmid pSB1 was also obtained from Japan Tobacco Inc. *E. coli* strain HB101 containing pPHP8904 was mated with Agrobacterium strain LBA4404 harboring pSB 1 to create the cointegrate plasmid in Agrobacterium, designated as LBA4404(pPHP10525) as shown in FIG. 1*c*, using the method of Ditta et al., (*Proc. Natl. Acad. Sci. USA* 77:7347–7351, 1980). LBA4404(pPHP10525) was selected based on resistance of transformed Agrobacterium to spectinomycin and verified as a recombinant by a SalI restriction digest of the plasmid.

EXAMPLE 2

Transformation of A188 using the Protocol of Ishida et al.

Transformation of A188 was performed according to the protocol of Ishida et al. except that 1.5 mg/l bialaphos was used during the first two weeks of the selection step while 3 mg/l bialaphos was used for the remainder of the selection period (Ishida et al. used 5 mg/l phosphinothricin (PPT) during the first two weeks of selection and 10 mg/l PPT during the remainder of the selection period). Use of bialaphos compared to PPT resulted in a lower initial frequency of recovery of callus lines growing on herbicide and plants regenerated on herbicide, but the final frequency of confirmed transformed plants, as determined by expression of the introduced GUS gene, is similar using the two herbicides. This difference can be attributed to the tighter selection achieved using bialaphos rather than PPT. PPT leads to a higher number of escapes, i.e., plants regenerated from herbicide-selected callus that are not actually transformed (Dennehey et al. *Plant Cell, Tissue and Organ Culture* 36:1–7, 1994). Therefore, in all subsequent experiments, bialaphos was used as the selective agent. The same source of A188 seed was used as that of Ishida et at. The Agrobacterium strain used was LBA4404(PHP 10525), which was identical to the strain used in Ishida et al. except 2X35S-bar replaced 35S-bar and Ubi-intron-GUS replaced 35S-intron-GUS (Details are provided in Example 1). The results of the transformation are summarized in Table 3. The proportion of embryos which produced herbicide-resistant callus and the proportion of embryos which produced regenerated plants was higher using the modified method of Ishida et al. (compare Tables 1 and 3), although the final stable transformation frequencies are similar (compare B/A in Table 1 and Table 3). This result can be attributed to the tendency for tighter selection and fewer escapes when bialaphos is used rather than PPT. GUS+ plants refer to those plants which showed positive expression of the GUS gene, as determined by the standard X-gluc assay (McCabe, D. E., 1988, *Biotechnol.* 6:923–926).

TABLE 3

Transformation of A188 using the protocol of Ishida et al.

| Experiment No. | Inoculated (A) | Callus growing on herbicide | Plants regenerated on herbicide | GUS+ plants (B) | Frequency (B/A %) |
| --- | --- | --- | --- | --- | --- |
| 1 | 150 | 28 | 20 | 16 | 10.7% |
| 2 | 180 | 21 | 19 | 16 | 8.9% |
| 3 | 50 | 9 | 9 | 9 | 18.0% |
| 4 | 157 | 28 | 18 | 16 | 10.2% |

As demonstrated in Table 3, the range of transformation frequencies was within the range reported by Ishida et al.

EXAMPLE 3

Transformation of Hi-II using the Protocol of Ishida et al.

The protocols of Ishida et al. (supra) were used in this Example. As in Example 2, bialaphos was substituted for PPT. The Agrobacterium strain LBA4404(pPHP10525) described in Example 1 and used in Example 2 was also used in this Example. "Hi-II" was derived by reciprocal crosses between plants of Hi-II Parent A and plants of Hi-II Parent B (both parents available from the Maize Genetic Cooperation Stock Center, Univ. of Illinois at Champaign/Urbana, Ill.). Seeds recovered from the crosses were termed Hi-II seeds. Hi-II seeds were planted either in a greenhouse or a field. The resulting Hi-II plants were either self-pollinated or cross-pollinated with sister plants. Immature embryos were isolated from ears harvested between about 9–13 days after pollination. The embryos used for these experiments were generally in the 1.0–1.2 mm size range. GUS+ events were determined at the callus stage or regenerated plant stage. The results using the Ishida et al. protocol (see summary of protocol in Table 2) are summarized in Table 4.

TABLE 4

Results on transformation of Hi-II using the protocol of Ishida et al.

| | Number of Immature Embryos | | |
| --- | --- | --- | --- |
| Experiment No. | Inoculated | Produced GUS+ events | Frequency |
| 1 | 165 | 4 | 2.4% |
| 2 | 30 | 1 | 3.3% |
| 3 | 205 | 6 | 2.9% |
| 4 | 87 | 1 | 1.1% |
| 5 | 177 | 8 | 4.5% |

TABLE 4-continued

Results on transformation of Hi-II using the protocol of Ishida et al.

| | Number of Immature Embryos | | |
| --- | --- | --- | --- |
| Experiment No. | Inoculated | Produced GUS+ events | Frequency |
| 6 | 56 | 4 | 7.1% |
| 7 | 80 | 1 | 1.3% |
| 8 | 120 | 1 | 0.8% |
| 9 | 115 | 5 | 4.3% |
| 10 | 58 | 4 | 6.9% |

The results indicated that the transformation frequencies for Hi-II (a cross between A188 and B73) were within the range reported by Ishida et al. for crosses of A188 with a variety of other inbreds and provided a basis for comparing other transformation protocols.

EXAMPLE 4

Transformation of Hi-II using PHI Protocols

Preparation of Agrobacterium suspension: Agrobacterium was streaked out from a-80° frozen aliquot onto a plate containing PHI-L medium and cultured at 28° C. in the dark for 3 days. PHI-L media comprised 25 ml/l Stock Solution A, 25 ml/l Stock Solution B, 450.9 ml/l Stock Solution C and spectinomycin (Sigma Chemicals) added to a concentration of 50 mg/l in sterile ddH$_2$O (stock solution A: K$_2$HPO$_4$ 60.0 g/l, NaH$_2$PO$_4$ 20.0 g/l, adjust pH to 7.0 w/KOH and autoclave; stock solution B: NH$_4$Cl 20.0 g/l, MgSO$_4$.7H$_2$O 6.0 g/l, KCl 3.0 g/l, CaCl$_2$ 0.20 g/l, FeSO$_4$.7H$_2$O 50.0 mg/l, autoclave; stock solution C: glucose 5.56 g/l, agar 16.67 g/l (#A-7049, Sigma Chemicals, St. Louis, Mo.) and autoclave).

The plate can be stored at 4° C. and used usually for about 1 month. A single colony was picked from the master plate and streaked onto a plate containing PHI-M medium [yeast extract (Difco) 5.0 g/l; peptone (Difco) 10.0 g/l; NaCl 5.0 g/l; agar (Difco) 15.0 g/l; pH 6.8, containing 50 mg/L spectinomycin] and incubated at 28° C. in the dark for 2 days.

Five ml of either PHI-A, [CHU(N6) basal salts (Sigma C-1416) 4.0 g/l, Eriksson's vitamin mix (1000X, Sigma-1511) 1.0 ml/l; thiamine.HCl 0.5 mg/l (Sigma); 2,4-dichlorophenoxyacetic acid (2,4-D, Sigma) 1.5 mg/l; L-proline (Sigma) 0.69 g/l; sucrose (Mallinckrodt) 68.5 g/l; glucose (Mallinckrodt) 36.0 g/l; pH 5.2] for the PHI basic medium system, or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1.0 g/l; 2, 4-D 1.5 mg/l; sucrose 68.50 g/l; glucose 36.0 g/l; adjust pH to 5.2 w/KOH and filter-sterilize] for the PHI combined medium system and 5 $\mu$l of 100 mM (3'-5'-Dimethoxy-4'-hydroxyacetophenone, Aldrich chemicals) were added to a 14 ml Falcon tube in a hood. About 3 full loops (5 mm loop size) Agrobacterium was collected from the plate and suspended in the tube, then the tube was vortexed to make an even suspension. One ml of the suspension was transferred to a spectrophotometer tube and the OD of the suspension was adjusted to 0.72 at 550 nm by adding either more Agrobacterium or more of the same suspension medium. The Agrobacterium concentration was approximately 1×10$^9$ cfu/ml. The final Agrobacterium suspension was aliquoted into 2 ml microcentrifuge tubes, each containing 1 ml of the suspension. The suspensions were then used as soon as possible.

Embryo Isolation, Infection and Co-Cultivation

About 2 ml of the same medium (here PHI-A or PHI-I) used for the Agrobacterium suspension were added into a 2 ml microcentrifuge tube. Immature embryos were isolated from a sterilized ear with a sterile spatula (Baxter Scientific Products S1565) and dropped directly into the medium in the tube. A total of about 100 embryos were placed in the tube. The optimal size of the embryos was about 1.0–1.2 mm. The cap was then closed on the tube and the tube was vortexed with a Vortex Mixer (Baxter Scientific Products S8223-1) for 5 sec. at maximum speed. The medium was removed and 2 ml of fresh medium were added and the vortexing repeated. All of the medium was drawn off and 1 ml of Agrobacterium suspension was added to the embryos and the tube vortexed for 30 sec. The tube was allowed to stand for 5 min. in the hood. The suspension of Agrobacterium and embryos was poured into a Petri plate containing either PHI-B medium [CHU(N6) basal salts (Sigma C-1416) 4.0 g/l; Eriksson's vitamin mix (1000X, Sigma-1511) 1.0 ml/l; thiamine.HCl 0.5 mg/l; 2.4-D 1.5 mg/l; L-proline 0.69 g/l; silver nitrate 0.85 mg/l; gelrite (Sigma) 3.0 g/l; sucrose 30.0 g/l; acetosyringone 100 $\mu$M; pH 5.8], for the PHI basic medium system, or PHI-J medium [MS Salts 4.3 g/l; nicotinic acid 0.50 mg/l; pyridoxine HCl 0.50 mg/l; thiamine.HCl 1.0 mg/l; myo-inositol 100.0 mg/l; 2, 4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 $\mu$M acetosyringone with a final pH of 5.8 for the PHI combined medium system. Any embryos left in the tube were transferred to the plate using a sterile spatula. The Agrobacterium suspension was drawn off and the embryos placed axis side down on the media. The plate was sealed with Parafilm tape or Pylon Vegetative Combine Tape (product named "E.G.CUT" and is available in 18 mm×50 m sections; Kyowa Ltd., Japan) and incubated in the dark at 23–25° C. for about 3 days of co-cultivation.

Resting, Selection and Regeneration Steps

For the resting step, all of the embryos were transferred to a new plate containing PHI-C medium [CHU(N6) basal salts (Sigma C-1416) 4.0 g/l; Eriksson's vitamin mix (1000X Sigma-151 1) 1.0 ml/l; thiamine.HCl 0.5 mg/l; 2.4-D 1.5 mg/l; L-proline 0.69 g/l; sucrose 30.0 g/l; MES buffer (Sigma) 0.5 g/l; agar (Sigma A-7049, purified) 8.0 g/l; silver nitrate 0.85 mg/l; carbenicillin 100 mg/l; pH 5.8]. The plate was sealed with Parafilm or Pylon tape and incubated in the dark at 28° C. for 3–5 days.

For selection, all of the embryos were then transferred from the PHI-C medium to new plates containing PHI-D medium, as a selection medium, [CHU(N6) basal salts (SIGMA C-1416) 4.0 g/l; Eriksson's vitamin mix (1000X, Sigma-1511) 1.0 ml/l; thiamine.HCl 0.5 mg/l; 2.4-D 1.5 mg/l; L-proline 0.69 g/l; sucrose 30.0 g/l; MES buffer 0.5 g/l; agar (Sigma A-7049, purified) 8.0 g/l; silver nitrate 0.85 mg/l; carbenicillin (ICN, Costa Mesa, Calif.) 100 mg/l; bialaphos (Meiji Seika K. K., Tokyo, Japan) 1.5 mg/l for the first two weeks followed by 3 mg/l for the remainder of the time.; pH 5.8] putting about 20 embryos onto each plate. The plates were sealed as described above and incubated in the dark at 28° C. for the first two weeks of selection. The embryos were transferred to fresh selection medium at two week intervals. The tissue was subcultured by transferring to fresh selection medium for a total of about 2 months. The herbicide-resistant calli were then "bulked up" by growing on the same medium for another two weeks until the diameter of the calli was about 1.5–2 cm.

For regeneration, the calli were then cultured on PHI-E medium [MS salts 4.3 g/l; myo-inositol 0.1 g/l; nicotinic acid 0.5 mg/l, thiamine.HCl 0.1 mg/l, Pyridoxine.HCl 0.5 mg/l, Glycine 2.0 mg/l, Zeatin 0.5 mg/l, sucrose 60.0 g/l, Agar (Sigma, A-7049) 8.0 g/l, Indoleacetic acid (IAA, Sigma) 1.0 mg/l, Abscisic acid (ABA, Sigma) 0.1 $\mu$M, Bialaphos 3 mg/l, carbenicillin 100 mg/l adjusted to pH 5.6] in the dark at 28° C. for 1–3 weeks to allow somatic embryos to mature. The calli were then cultured on PHI-F medium (MS salts 4.3 g/l; myo-inositol 0.1 g/l; Thiamine.HCl 0.1 mg/l, Pyridoxine.HCl 0.5 mg/l, Glycine 2.0 mg/l, nicotinic acid 0.5 mg/l; sucrose 40.0 g/l; gelrite 1.5 g/l; pH 5.6] at 25° C. under a daylight schedule of 16 hrs. light (270 uE $m^{-2}sec^{-1}$) and 8 hrs. dark until shoots and roots developed. Each small plantlet was then transferred to a 25×150 mm tube containing PHI-F medium and grown under the same conditions for approximately another week. The plants were transplanted to pots with soil mixture in a greenhouse. GUS+ events were determined at the callus stage or regenerated plant stage. The results are summarized in Table 5.

For Hi-II a preferred optimized protocol was $0.5\times10^9$ cfu/ml Agrobacterium (Table 6), a 3–5 day resting step (Example 5), and no $AgNO_3$ in the infection medium (PHI-A medium). The examples of this invention provide a variety of experiments that similarly teach those of ordinary skill in the art to optimize transformation frequencies for other maize lines.

TABLE 5

Results on transformation of Hi-II using the PHI protocols

| Medium | Experiment No. | Number of Immature Embryos Inoculated | Produced GUS+ events | Frequency |
|---|---|---|---|---|
| PHI basic | 1 | 195 | 64 | 32.8% |
|  | 2 | 97 | 37 | 38.1% |
|  | 3 | 65 | 30 | 46.2% |
|  | 4 | 103 | 52 | 50.5% |
| PHI combined | 1 | 65 | 5 | 7.7% |
|  | 2 | 51 | 4 | 7.8% |
|  | 3 | 98 | 22 | 22.4% |
|  | 4 | 71 | 8 | 11.3% |

The results indicated that the PHI-combined medium system gave higher transformation frequencies than Ishida's protocol. On average, 13.7% stable transformants were generated with the PHI combined medium system, while 3.2% stable transformants were produced using the protocol of Ishida et al. Thus, the PHI combined medium system was about 4.3 times better than the Ishida et al. Protocol for Hi-II transformation. The transformation frequency was also very high with the PHI basic medium system producing transformation frequencies that were about 12.4 times better than the Ishida et al. protocol.

Experiments were also designed to develop a method for optimizing the concentration of Agrobacterium to be used for maize transformation. The same procedures were used as described for the experiments summarized in Table 5, with the following modifications in Agrobacterium preparation methods. For final concentrations of Agrobacterium other than $1\times10^9$ cfu/ml, a concentrated Agrobacterium suspension can initially be made. The concentration of the Agrobacterium suspensions is determined by measuring the OD value at 550 nm of a dilution or serial dilution that gives a reading of approximately $OD_{550}=0.72$. The concentration of the Agrobacterium suspensions are then adjusted to the desired concentration for use in transformation experiments.

In the experiments summarized in Table 6, the working suspension of Agrobacterium used were $10\times10^9$, $2\times10^9$, $1\times10^9$, $0.5\times10^9$, $0.1\times10^9$ (all in cfu/ml) and GUS+ events were determined at the callus stage or regenerated plant stage. The results are shown in Table 6.

The results of Table 6 indicated that for both medium systems, transformation frequency was affected by Agrobacterium concentration. The highest transformation frequency was obtained using $0.5\times10^9$ cfu/ml Agrobacterium at the infection step for both medium systems for Hi-II embryos. The transformation frequency with $0.5\times10^9$ cfu/ml and PHI-basic medium system as provided in Table 6 is not as high as the transformation frequency in Table 5, because an old version of PHI-A (containing $AgNo_3$, 2.0 mg/l 2,4-D, at pH 5.8) was used in the experiments with results provided in Table 6. It is likely that the transformation frequencies for the PHI-basic medium system could be improved by removing $AgNO_3$ in the infection medium and using 1.5 mg/l 2-4,D with the infection medium at pH 5.2.

in Examples 3. As described in Example 2, the Ishida et al. protocol was identical to that described by Ishida et al. (supra) except that bialaphos replaced PPT.

The PHI basic medium system was identical to that described in Example 4 except that PHI-A medium additionally included 0.85 mg/l $AgNO_3$, another 0.5 mg/l 2,4-D at pH 5.8 for the infection step. PHI-D medium was prepared as described in Example 4 but without proline or MES buffer. An additional 0.5 mg/l 2,4-D was added in the selection step. In addition, 3 g/l gelrite was used to replace agar in the selection medium. The PHI combined medium system was also identical to that of Example 4 except that proline and MES buffer were not added to the PHI-D medium and 2,4-D was used at a concentration of 2.0 mg/l and 3 g/l of Gelrite was used to replace the agar in the selection step. Results are provided in Table 7 below.

Results indicated that the addition of a 4-day resting step can increase the transformation frequency about 2.7 times as compared with the Ishida et al. method. The 4-day resting

TABLE 6

Results of experiments to optimize Agrobacterium concentrations

Agrobacterium Concentration (cfu/ml)

| Med. | Exp. No. | $1 \times 10^{10}$ Embryos | | | $2 \times 10^9$ Embryos | | | $1 \times 10^9$ Embryos | | | $0.5 \times 10^9$ Embryos | | | $0.1 \times 10^9$ Embryos | | |
|---|---|---|---|---|---|---|---|---|---|---|---|---|---|---|---|---|
| | | Inoculated | GUS+ events | % | Inoculated | GUS+ events | % | Inoculated | GUS+ events | % | Inoculated | GUS+ events | % | Inoculated | GUS+ events | % |
| PHI comb. | 1 | 138 | 1 | 0.7 | 64 | 2 | 3.1 | 66 | 2 | 3.0 | 51 | 4 | 7.8 | | ND* | |
| | 2 | 86 | 1 | 1.2 | 58 | 1 | 1.7 | 55 | 4 | 7.3 | 65 | 5 | 7.7 | | | |
| | 3 | 85 | 6 | 7.1 | 58 | 3 | 5.2 | 50 | 3 | 6.0 | 98 | 22 | 22.4 | | | |
| | 4 | 192 | 13 | 6.8 | 67 | 4 | 6.0 | 71 | 8 | 11.3 | | | | | | |
| PHI basic | 1 | | ND* | | | ND* | | 88 | 3 | 3.4 | 127 | 27 | 21.3 | 150 | 16 | 10.7 |
| | 2 | | | | | | | 134 | 9 | 6.7 | 86 | 15 | 17.4 | 242 | 17 | 70 |
| | 3 | | | | | | | 110 | 9 | 8.2 | 280 | 21 | 7.5 | 97 | 5 | 52 |
| | 4 | | | | | | | 85 | 2 | 2.4 | 196 | 15 | 7.7 | | | |

*Experiment not performed

EXAMPLE 5

Hi-II Transformation Including a Resting Step

Hi-II embryos were isolated and transformed as provided in Examples 3 and 4. The experiments compared PHI basic and PHI combined media systems with or without a four day resting step and contrasted the data to matched experiments using the transformation protocol of Ishida et al. as provided step increased the transformation frequency in the PHI combined medium system about 2.3 times. However, unexpectedly, the combination of the PHI basic protocol combined with a resting step resulted in an increase in the transformation frequency of about 15 times the frequency observed without a resting step. The combination of the protocols of this invention with a resting for Hi-II provided a significant improvement in transformation frequency.

TABLE 7

Hi-II Transformation With or Without Resting Step

| Transformation Protocol | Experiment No. | Without resting step | | | With 4-day resting | | |
|---|---|---|---|---|---|---|---|
| | | Inoculated Embryos | Embryos producing GUS+ events | Frequency | Inoculated Embryos | Embryos producing GUS+ events | Frequency |
| Ishida et al. | 1 | 165 | 4 | 2.4% | 177 | 11 | 6.2% |
| | 2 | 30 | 1 | 3.3% | 56 | 5 | 8.9% |
| | Total | 195 | 5 | 2.6% | 233 | 16 | 6.9% |
| PHI basic | 1 | 154 | 1 | 0.6% | 50 | 8 | 16.0% |
| | 2 | 108 | 1 | 0.9% | 47 | 3 | 6.4% |
| | 3 | | | | 45 | 10 | 22.2% |
| | 4 | | | | 38 | 1 | 2.6% |
| | Total | 262 | 2 | 0.8% | 180 | 22 | 12.2% |
| PHI | 1 | 170 | 14 | 8.2% | 66 | 2 | 3.0% |

TABLE 7-continued

Hi-II Transformation With or Without Resting Step

| Transformation Protocol | Experiment No. | Without resting step | | | With 4-day resting | | |
|---|---|---|---|---|---|---|---|
| | | Inoculated Embryos | Embryos producing GUS+ events | Frequency | Inoculated Embryos | Embryos producing GUS+ events | Frequency |
| combined | 2 | 64 | 0 | 0.0% | 55 | 4 | 7.3% |
| | 3 | 230 | 0 | 0.0% | 50 | 3 | 6.0% |
| | 4 | | | | 71 | 8 | 11.3% |
| | Total | 464 | 14 | 3.0% | 242 | 17 | 7.0% |

EXAMPLE 6

Transformation of A188 x Inbred Crosses using the PHI Protocols $F_1$ immature embryos were isolated from crosses of A188 to other inbreds and were subjected to transformation by Agrobacterium. The protocols used were the same as in Example 4, with the following modifications. The Agrobacterium suspension was prepared with either the N6 salt containing medium, PHI-G [100 ml/l of a 10X solution of N6 macronutrients (463.0 mg/l $(NH_4)_2SO_4$, 400.0 mg/l $KH_2PO_4$, 125.33 mg/l $CaCl_2$, 90.37 mg/l $MgSO_4$ and 2,830.0 mg/l $KNO_3$), 2.44 mg/l Boric acid, 37.1 mg/l $Na_2$-EDTA.$2H_2O$, 27.88 mg/l $FeSO4.7H_2O$, 7.33 mg/l $MnSO_4.H_2O$, 0.77 mg/l KI, 0.6 mg/l $ZnSO_4.7H_2O$, 0.15 mg/l $Na_2MoO_2.2H_2O$, 1.68 g/l $KNO_3$, 0.8 mg/l glycine, 3.2 mg/l nicotinic acid, 3.2 mg/l Pyridoxine.HCl, 3.4 mg/l Thiamine.HCl, 0.6 g/l Myo-inositol, 0.8 mg/l 2,4-D, 1.2 mg/l Dicamba (Sigma), 1.98 g/l L-proline, 0.3 g/l casein hydrolysate, 68.5 g/l sucrose and 36.0 g/l glucose, pH 5.2] or the MS salt-containing medium, PHI-I (supra) for the infection step. The co-cultivation medium was PHI-J (supra) and the co-cultivation time was about 3 to about 7 days. For PHJ90×A188, PHI-C medium (supra) was used in a 3 day resting step and PHI-D medium (supra) was used for selection. For PHN46×A188 and PHPP8×A188 transformations, no resting step was used, the co-cultivation time was about 5–7 days, and PHI-H medium [100 ml/l of a 10X solution of N6 macronutrients (463.0 mg/l $(NH_4)_2SO_4$, 400.0 mg/l $KH_2PO_4$, 125.33 mg/l $CaCl_2$, 90.37 mg/l $MgSO_4$ and 2,830.0 mg/l $KNO_3$), 2.44 mg/l Boric acid, 37.1 mg/l $Na_2$-EDTA.$2H_2O$, 27.88 mg/l $FeSO4.7H_2O$, 7.33 mg/l $MnSO_4.H_2O$, 0.77 mg/l KI, 0.6 mg/l $ZnSO_4.7H_2O$, 0.15 mg/l $Na_2MoO_2.2H_2O$, 1.68 g/l $KNO_3$, 0.8 mg/l glycine, 3.2 mg/l nicotinic acid, 3.2 mg/l Pyridoxine.HCl, 3.4 mg/l Thiamine.HCl, 0.6 g/l Myo-inositol, 1.0 mg/l 2,4-D, 1.0 mg/l Dicamba, 0.3 g/l casein hydrolysate, 20.0 g/l Sucrose, 0.6 g/l glucose, 0.5 g/l MES buffer, 1 mg/l $AgNO3$, 5 mg/l bialaphos, 100 mg/l carbenicillin and 8.0 g/l Agar (Sigma A-7049, purified); pH 5.8] was used for selection. GUS+ events were determined at the callus stage or could be determined at the regenerated plant stage. The results are summarized in Table 8.

These results indicate that the methods of this invention produced an improved transformation frequency for crosses of A188 to the inbreds with transformation frequencies ranging from about 6.9% to 50.5% (citing data including the Hi-II studies from Table 5). These transformation frequencies were significantly higher than the frequencies reported by Ishida et al. for A188×inbred crosses which ranged from about 0.4 to 5.3%.

TABLE 8

Results of transformation of A188 x inbred crosses using the PHI protocols

| Variety | Experiment No. | Number of Immature Embryos | | |
|---|---|---|---|---|
| | | Inoculated | Produced GUS+ events | Frequency |
| PHJ90 × A188 | 1 | 151 | 72 | 47.7% |
| | 2 | 85 | 36 | 42.4% |
| PHN46 × A188 | 1 | 112 | 46 | 41.1% |
| | 2 | 80 | 37 | 46.3% |
| | 3 | 114 | 47 | 41.2% |
| | 4 | 51 | 8 | 15.7% |
| PHPP8 × A188 | 1 | 160 | 11 | 6.9% |
| | 2 | 109 | 8 | 7.3% |
| | 3 | 141 | 27 | 19.1% |

EXAMPLE 7

Transformation of Elite Inbreds using the PHI Protocols

For transformation of elite inbred lines, the protocols described in Example 4 were used, with the following modifications. For PHJ90, the Agrobacterium suspension was prepared with either PHI-A (PHI basic medium) or PHI-I (PHI combined medium), the co-cultivation medium was either PHI-B (PHI basic medium) or PHI-J (PHI combined medium), the co-cultivation time was about 3 to 5 days, PHI-C medium was used for a resting step of about 3–5 days, and PHI-D medium was used for selection. For PHN46, the Agrobacterium suspension was prepared with either PHI-G or PHI-I (both PHI combined media), the co-cultivation media was PHI-J, the co-cultivation time was about 7 days, no resting step was used, and PHI-H medium was used for selection. For PHP38, the Agrobacterium suspension was prepared with PHI-I (PHI combined media), the co-cultivation medium was PHI-J, the co-cultivation time was about 3 days, PHI-H without bialaphos was used for a resting step of about 4 days and PHI-H medium was used for selection. Formulations for the media referenced in this example are detailed in either Example 4–6. GUS+ events were determined at the regenerated plant stage. The results are summarized in Table 9. Using the protocol of Ishida, et al., no stable transformants were recovered from 594 embryos in 5 separate experiments for PHJ90, 644 embryos in 4 separate experiments for PHN46, and 263 embryos in 4 separate experiments for PHP38.

TABLE 9

Results on transformation of elite inbreds using the PHI protocols

| Variety | Experiment No. | Number of Immature Embryos Inoculated | Produced GUS+ plants | Frequency |
|---|---|---|---|---|
| PHJ90 | 1 | 85 | 1 | 1.2% |
| | 2 | 58 | 1 | 1.7% |
| | 3 | 164 | 2 | 1.2% |
| | 4 | 60 | 3 | 5.0% |
| PHN46 | 1 | 44 | 3 | 6.8% |
| | 2 | 49 | 4 | 8.2% |
| | 3 | 114 | 8 | 7.0% |
| | 4 | 123 | 11 | 8.9% |
| PHP38 | 1 | 89 | 2 | 2.2% |
| | 2 | 104 | 1 | 1.0% |
| | 3 | 116 | 1 | 0.9% |

The results demonstrated that both the PHI basic medium and the PHI combined medium which use N6 salts for various steps in the protocols and carbenicillin led to recovery of stably transformed calli and plants (Table 9), at frequencies from ~1.0% to 9.0%. Each of these inbred lines belongs to a different heterotic group, so the methods of the present invention enable one not only to transform inbred lines across a wide range of genotypes and to transform inbred lines of commercial importance. Some inbreds (e.g., PHN46) could be transformed without a resting step, but the resting step was important for some inbreds such as PHJ90. Those skilled in the art will recognize that the transformation protocols of this invention can be performed in duplicate with or without the addition of a resting step without undue experimentation. These results are significant because they demonstrate that the methods of this invention can be used to transform a variety of elite lines.

The effect of various combinations of co-cultivation periods and resting periods were also reviewed for these elite inbreds and the results of these experiments are summarized below:

TABLE 10

Combinations of Co-cultivation and Resting Time for Elite Inbreds

| Inbred | Length of Co-cultivation (days) | Length of Resting (days) | Transformation Frequency Range (%) |
|---|---|---|---|
| PHN46 | 3 | 0 | 0.6–3.4 |
| | 5 | 0 | 2 |
| | 7 | 0 | 0.6–8.9 |
| | 10 | 0 | 1.4–3.4 |
| PHP38 | 3 | 4 | 0.9–2.2 |
| | 7 | 0 | 2.2–14.5 |
| PHJ90 | 3 | 0 | 0 |
| | 3 | 3 | 0.6–1.2 |
| | 3 | 4 | 1.2–1.7 |

These data indicates that the resting step is important for some inbreds using a 3 day co-cultivation period but that longer co-cultivation periods may compensate for the absence of a resting step since the resting step, like the co-cultivation step, provides a period of time for the embryo to be cultured in the absence of a selective agent. Those of ordinary skill in the art can readily test combinations of co-cultivation and resting times to optimize or improve the transformation frequency of other inbreds without undue experimentation. Moreover, since these inbreds are representative of three different heterotic groups, these methods demonstrate that they can be extended to other heterotic groups or to additional inbreds within the heterotic groups represented here.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

What is claimed is:

1. A method for transforming maize using Agrobacterium comprising the steps of:
   contacting at least one immature embryo from a maize plant with Agrobacterium capable of transferring at least one gene to the embryo;
   co-cultivating the embryo with Agrobacterium;
   culturing the embryo in a medium comprising N6 salts, an antibiotic at concentrations capable of inhibiting the growth of Agrobacterium, and a selective agent to select for embryos expressing the gene; and
   regenerating plants expressing the gene.

2. The method of claim 1 wherein the plants are stably transformed.

3. The method of claim 1 wherein the gene is expressed in subsequent generations.

4. A method for transforming maize using Agrobacterium comprising the steps of:
   contacting at least one immature embryo from a maize plant with Agrobacterium capable of transferring at least one gene to the embryo in a medium comprising N6 salts;
   co-cultivating the embryo with Agrobacterium in a medium comprising N6 salts;
   culturing the embryo in a medium comprising N6 salts, an antibiotic at concentrations capable of inhibiting the growth of Agrobacterium, and a selective agent to select for embryos expressing the gene; and
   regenerating plants expressing the gene in a medium comprising MS salts.

5. The method of claim 4 wherein the plants are stably transformed.

6. The method of claim 4 wherein the gene is expressed in subsequent generations.

7. A method for transforming maize using Agrobacterium comprising the steps of:
   contacting at least one immature embryo from a maize plant with Agrobacterium capable of transferring at least one gene to the embryo in a medium comprising N6 or MS salts;
   co-cultivating the embryo with Agrobacterium in a medium comprising MS salts;
   culturing the embryo in a medium comprising N6 salts, an antibiotic at concentrations capable of inhibiting the growth of Agrobacterium, and a selective agent to select for embryos expressing the gene; and
   regenerating plants expressing the gene in a medium comprising MS salts.

8. The method of claim 7 wherein the plants are stably transformed.

9. The method of claim 7 wherein the gene is expressed in subsequent generations.

10. A method for optimizing the production of transgenic maize plants of a first genotype using Agrobacterium-mediated transformation comprising the steps of:

isolating immature embryos from maize;

separating the embryos into treatment groups;

incubating each treatment group separately in a medium comprising N6 or MS salts and in a suspension of Agrobacterium at concentrations ranging from about $1\times10^8$ cfu/ml to about $1\times10^{10}$ cfu/ml;

co-cultivating the embryos with Agrobacterium on a solid medium;

culturing the embryos in a medium comprising N6 salts, an antibiotic at concentrations capable of inhibiting the growth of Agrobacterium, and a selective agent to select for embryos transformed by Agrobacterium;

identifying the treatment group with the highest transformation frequency; and using the concentration of Agrobacterium generating the highest transformation frequency to transform other embryos from the first genotype.

11. The method of claim 10 wherein the plants are stably transformed.

12. The method of claim 10 wherein the gene is expressed in subsequent generations.

13. A method for transforming maize using Agrobacterium comprising the steps of:

contacting at least one immature embryo from a maize plant with Agrobacterium capable of transferring at least one gene to the embryo;

co-cultivating the embryo with Agrobacterium;

culturing the embryo in a medium containing salts other than MS salts, an antibiotic at concentrations capable of inhibiting the growth of Agrobacterium, and a selective agent to select for embryos expressing the gene; and regenerating plants expressing the gene.

14. The method of claim 12 wherein the plants are stably transformed.

15. The method of claim 13 wherein the gene is expressed in subsequent generations.

16. The method of claim 1 wherein the contacting step additionally comprises contacting the immature embryos with Agrobacterium in a medium comprising N6 salts.

17. The method of claim 1 wherein the contacting step additionally comprises contacting the immature embryos with Agrobacterium in a medium comprising MS salts.

18. The method of claim 1 wherein the contacting step takes place in the absence of $AgNO_3$.

19. The method of claim 1 wherein the immature embryos are preferably from a size of about 0.3 mm to about 4 mm in length.

20. The method of claim 19 wherein the embryos are preferably about 0.8 mm to about 2.0 mm in length.

21. The method of claim 1 wherein the concentration of Agrobacterium is about $1\times10^8$ cfu/ml to about $1.5\times10^9$ cfu/ml.

22. The method of claim 21 wherein the Agrobacterium concentration is preferably from about $0.5\times10^9$ to about $1.0\times10^9$ cfu/ml.

23. The method of claim 1 wherein the contacting step takes place in a liquid suspension.

24. The method of claim 1 wherein the co-cultivation step takes place on a solid medium.

25. The method of claim 11 wherein a medium containing N6 salts is used in the co-cultivation step.

26. The method of claim 17 wherein a medium containing MS salts is used in the co-cultivation step.

27. The method of claim 1 wherein a medium containing MS salts is used in the regeneration step.

28. The method of claim 16 wherein a medium containing N6 salts is used in the co-cultivation and selection step.

29. The method of claim 17 wherein a medium containing MS salts is used in the co-cultivation step and a medium containing MS salts is used in the regeneration step.

30. The method of claim 1 additionally comprising the step of resting the embryos by culturing the embryos in medium containing an antibiotic capable of inhibiting the growth of Agrobacterium.

31. The method of claim 30 wherein the antibiotic is carbenicillin.

32. The method of claim 30 wherein the antibiotic in the selection step is carbenicillin.

33. The method of claim 31 wherein the concentration of carbenicillin is about 50 mg/l to about 250 mg/l.

34. The method of claim 31 wherein the concentration of carbenicillin is about 100 mg/l.

35. The method of claim 2 wherein the embryos are cultured for about 1 to about 15 days.

36. The method of claim 2 wherein the embryos are cultured for about 3 to about 5 days.

37. The method of claim 1 wherein the embryos are cultured in a PHI basic media system.

38. The method of claim 1 wherein the embryos are cultured in a PHI combined media system.

39. The method of claim 4 wherein the medium of the contacting step lacks $AgNO_3$.

40. The method of claim 4 wherein the Agrobacterium concentration is about $1\times10^8$ cfu/ml to about $1.5\times10^9$ cfu/ml.

41. The method of claim 40 wherein the Agrobacterium concentration is about $0.5\times10^9$ to about $1.0\times10^9$ cfu/ml.

42. The method of claim 4 wherein the contacting step takes place in a liquid and the co-cultivating and culturing steps take place on a solid medium.

43. The method of claim 4 additionally comprising the step of resting the embryo by culturing the embryo in a medium containing an antibiotic capable of inhibiting the growth of Agrobacterium.

44. The method of claim 43 wherein the antibiotic is carbenicillin.

45. The method of claim 7 wherein the medium of the contacting step lacks $AgNO_3$.

46. The method of claim 7 wherein the Agrobacterium concentration is about $1\times10^8$ cfu/ml to about $1.5\times10^9$ cfu/ml.

47. The method of claim 46 wherein the Agrobacterium concentration is about $0.5\times10^9$ to about $1.0\times10^9$ cfu/ml.

48. The method of claim 46 wherein the contacting step takes place in a liquid and the co-cultivating and culturing steps take place on a solid medium.

49. The method of claim 46 additionally comprising the step of resting the embryo by culturing the embryo in a medium containing an antibiotic capable of inhibiting the growth of Agrobacterium.

50. The method of claim 49 wherein the antibiotic is carbenicillin.

51. The method of claim 10 wherein the medium of the incubating step and the co-cultivating step is a medium comprising N6 salts.

52. The method of claim 10 wherein the medium of the incubating step is a medium comprising MS salts and the medium of the co-cultivating step is a medium comprising N6 salts.

53. The method of claim 10 wherein the medium of the incubating step is a medium comprising N6 salts and the medium of the co-cultivating step is a medium comprising MS salts.

54. The method of claim 10 additionally comprising the step of resting the embryo by culturing the embryo in a medium containing an antibiotic capable of inhibiting the growth of Agrobacterium.

55. The method of claim 10 wherein the antibiotic is carbenicillin.

56. The method of claim 10 wherein the combined length of the co-cultivating step and the resting step is at least three days.

57. The method of claim 54 wherein the length of the resting step is from 0 to about 10 days.

58. The method of claim 56 wherein the length of the resting step is about 3 to about 5 days.

59. The method of claim 4, wherein the media of the co-cultivating and/or culturing steps further comprises $AgNO_3$.

60. The method of claim 59 wherein the $AgNO_3$ is present in an amount in the range of from about 0.01 mg/l to about 200 mg/l.

61. The method of claim 7, wherein the media in the co-cultivating and/or culturing steps further comprises $AgNO_3$.

62. The method of claim 61 wherein the $AgNO_3$ is present in an amount in the range of from about 0.01 mg/l to about 200 mg/l.

* * * * *